(12) United States Patent
Sohn et al.

(10) Patent No.: US 10,443,078 B2
(45) Date of Patent: Oct. 15, 2019

(54) ***PICHIA KUDRIAVZEVII* NG7 MICROORGANISM AND USES THEREOF**

(71) Applicant: Korea Research Institute of Bioscience and Biotechnology, Daejeon (KR)

(72) Inventors: Jung Hoon Sohn, Daejeon (KR); Hyun Joo Park, Daejeon (KR); Sun Hee Lee, Daejeon (KR); Jung Hoon Bae, Daejeon (KR); Bong Hyun Sung, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 15/320,550

(22) PCT Filed: Jun. 22, 2015

(86) PCT No.: PCT/KR2015/006314
§ 371 (c)(1),
(2) Date: Aug. 15, 2017

(87) PCT Pub. No.: WO2015/194921
PCT Pub. Date: Dec. 23, 2015

(65) Prior Publication Data

US 2017/0349920 A1    Dec. 7, 2017

(30) Foreign Application Priority Data

Jun. 20, 2014    (KR) .................. 10-2014-0075461

(51) Int. Cl.
| | | |
|---|---|---|
| *C12N 9/04* | (2006.01) | |
| *C12N 1/19* | (2006.01) | |
| *C12P 7/56* | (2006.01) | |
| *C12P 7/06* | (2006.01) | |
| *C12P 7/40* | (2006.01) | |
| *C12N 9/88* | (2006.01) | |
| *C12R 1/84* | (2006.01) | |
| *C12N 1/16* | (2006.01) | |

(52) U.S. Cl.
CPC .................. *C12P 7/56* (2013.01); *C12N 1/16* (2013.01); *C12N 9/0006* (2013.01); *C12N 9/88* (2013.01); *C12P 7/06* (2013.01); *C12R 1/84* (2013.01); *C12Y 101/01027* (2013.01); *C12Y 401/01001* (2013.01); *C12Y 401/01023* (2013.01); *Y02E 50/17* (2013.01)

(58) Field of Classification Search
CPC .... C12N 9/0006; C12N 15/815; C12N 15/52; C12N 9/88; C12P 7/02; C12Y 101/02003
USPC .............. 536/23.2; 435/320.1, 139, 161, 136
See application file for complete search history.

(56) References Cited

U.S. PATENT DOCUMENTS

2009/0226989 A1    9/2009  Suominen et al.

FOREIGN PATENT DOCUMENTS

| JP | 2012-235729 A | 12/2012 |
|---|---|---|
| KR | 10-2008-0028902 A | 4/2008 |
| KR | 10-2014-0001165 A | 1/2014 |

OTHER PUBLICATIONS

Abdel-Rahman et al. (Apr. 24, 2013) "Recent advances in lactic acid production by microbial fermentation processes," Biotechnol. Adv. 31(6):877-902.
Dandi et al. (Nov. 21, 2012) "Bioprospecting of thermo- and osmo-tolerant fungi from mango pulp-peel compost for bioethanol production," Antonie Van Leeuwenhoek. 103(4):723-736.
Gallardo et al. (2011) "Enrichment of a continuous culture of *Saccharomyces cerevisiae* with the yeast Issatchenkia orientalis in the production of ethanol at increasing temperatures," J Ind Microbiol Biotechnol. 38(3):405-414.
Kitagawa et al. (2010) "Construction of a β-glucosidase expression system using the multistress-tolerant yeast Issatchenkia orientalis," Appl. Microbial. Biotechnol. 87(5):1841-1853.
Qiu et al. (1997) "The *Escherichia coli* polB locus is identical to dinA, the structural gene for DNA polymerase II. Characterization of Pol II purified from a polB mutant," Journal of Biological Chemistry. 272:8611-8617.
Sauer et al. (2010) "16 years research on lactic acid production with yeast—ready for the market?" Biotechnol Genet Eng Rev. 27:229-256.
Toivari et al. (Feb. 7, 2013) "Low pH D-xylonate production with Pichia kudriavzevii," Bioresour. Technol. 133:555-562.
International Search Report with Written Opinion corresponding to International Patent Application No. PCT/KR2015/006314, dated Sep. 24, 2015.

*Primary Examiner* — Robert B Mondesi
*Assistant Examiner* — Mohammad Y Meah
(74) *Attorney, Agent, or Firm* — Lathrop Gage LLP; Andrew T. Wilkins

(57) ABSTRACT

The present invention relates to: a novel *Pichia kudriavzevii* microorganism NG7 showing heat resistance and acid resistance; a composition, for producing organic acid or alcohol, which comprises the microorganism and a culture of the same; and a method, for producing an organic acid or alcohol, which comprises culturing the microorganism.

13 Claims, 18 Drawing Sheets

Specification includes a Sequence Listing.

[FIG. 1]
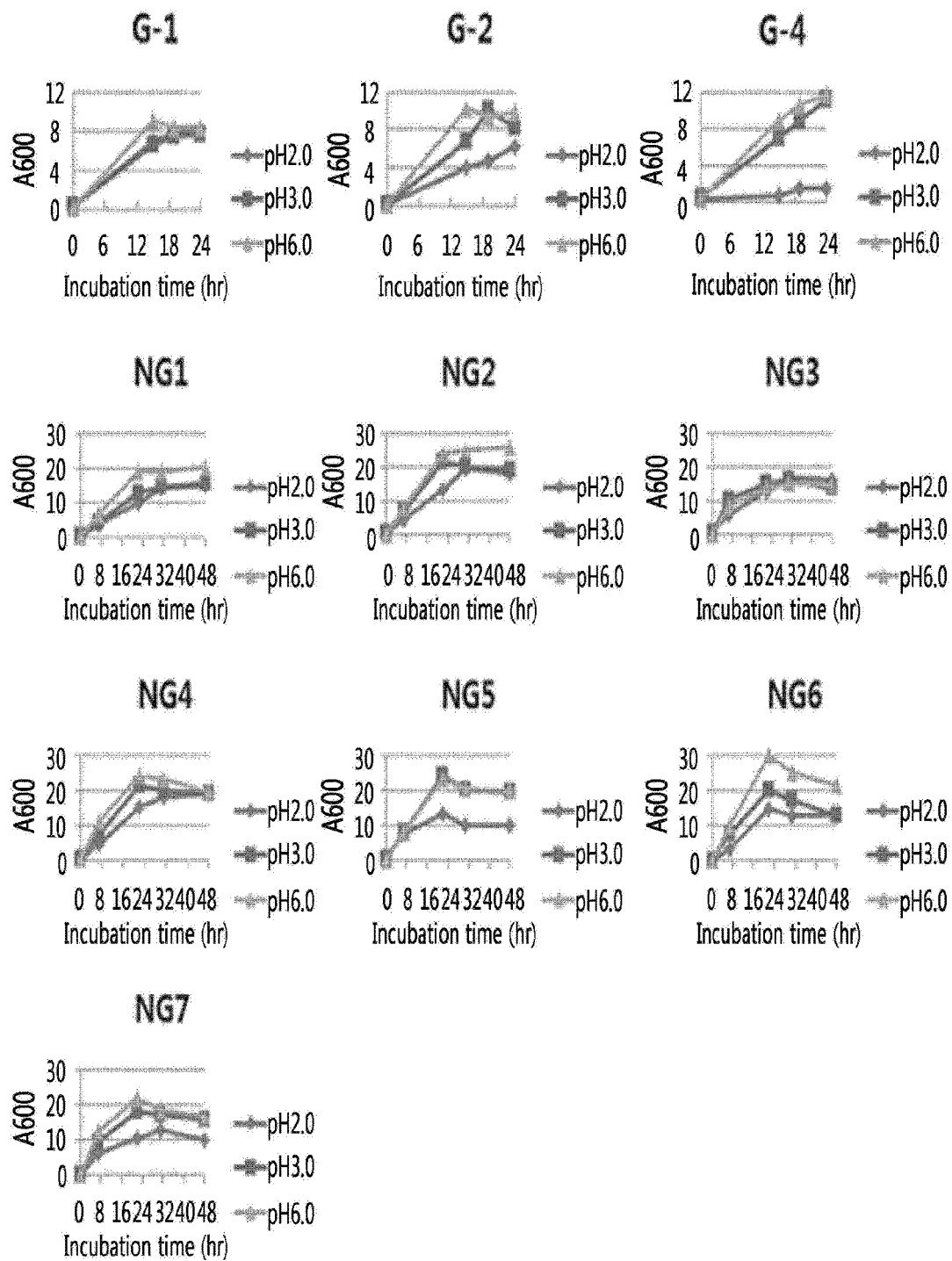

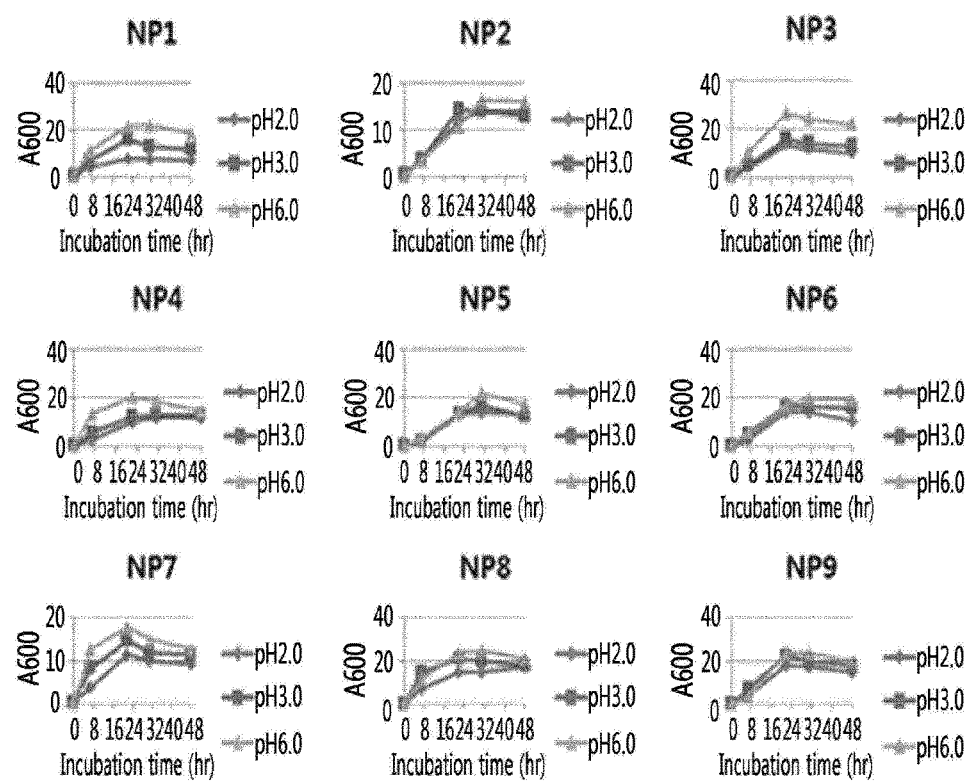
[FIG. 2]

[FIG. 3]
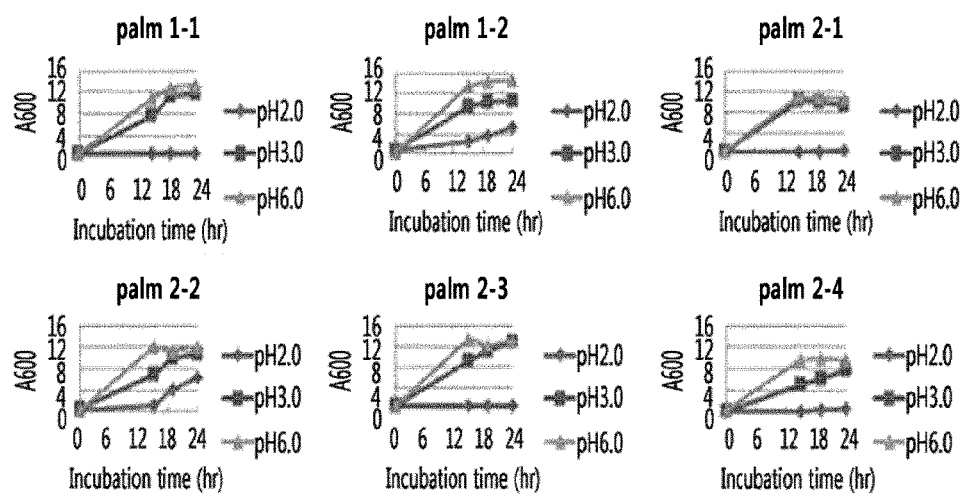

[FIG. 4]
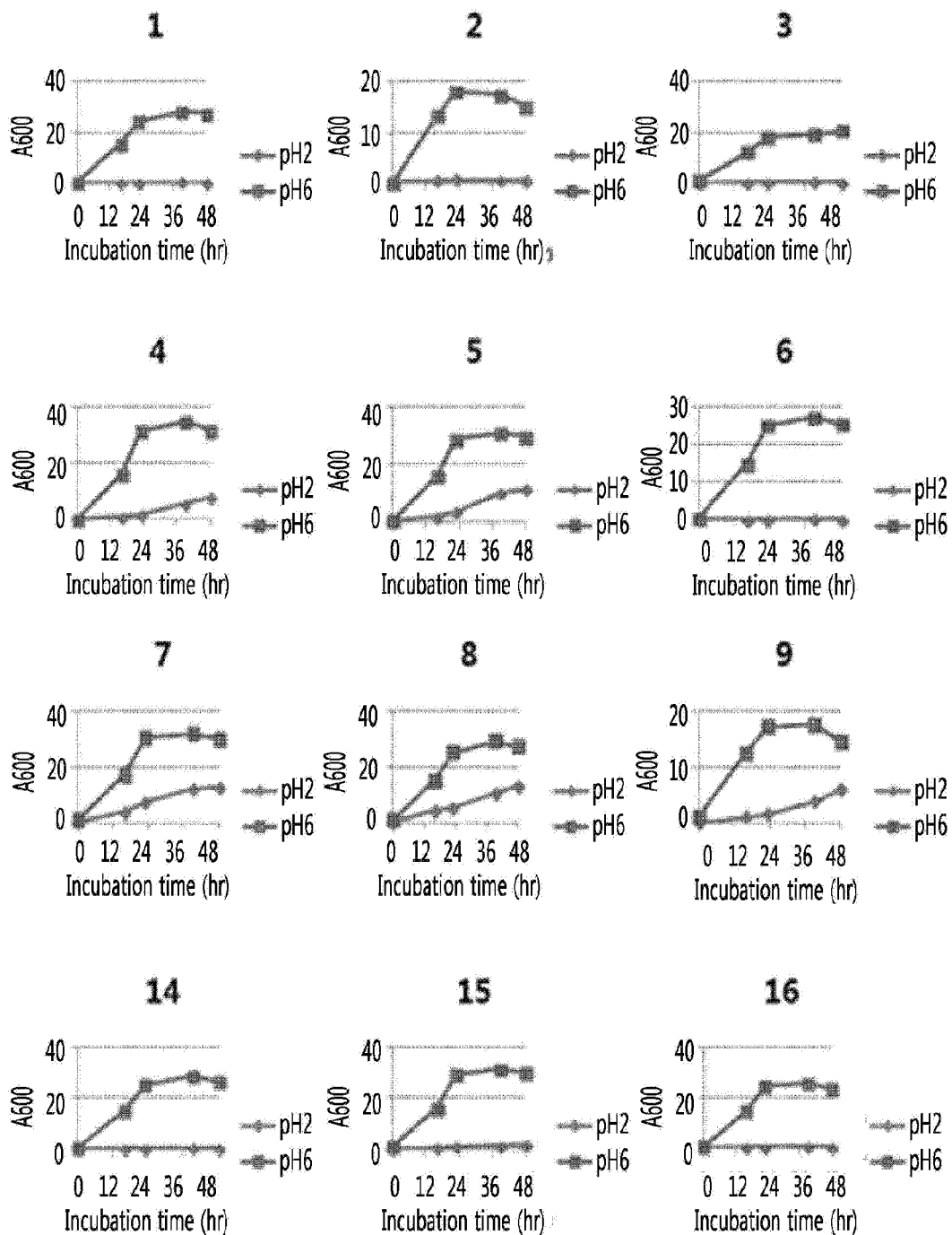

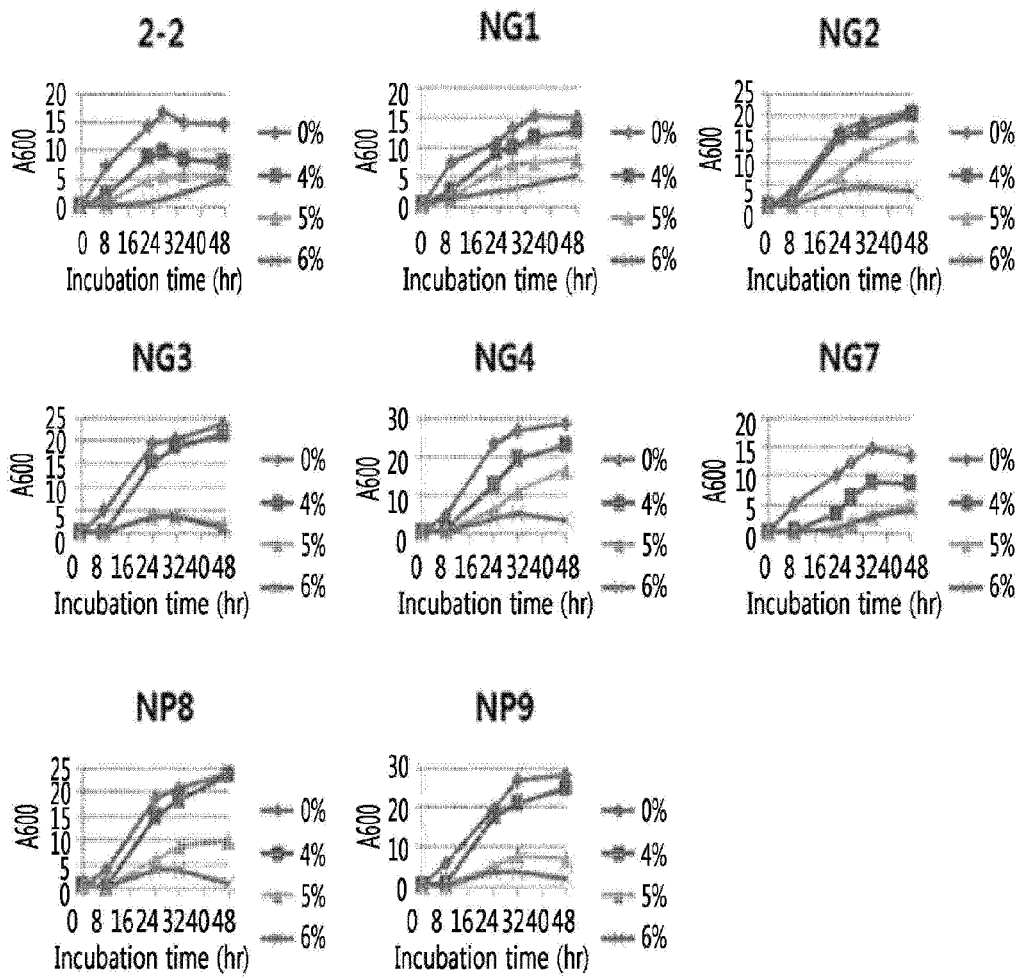
[FIG. 5]

[FIG. 6]
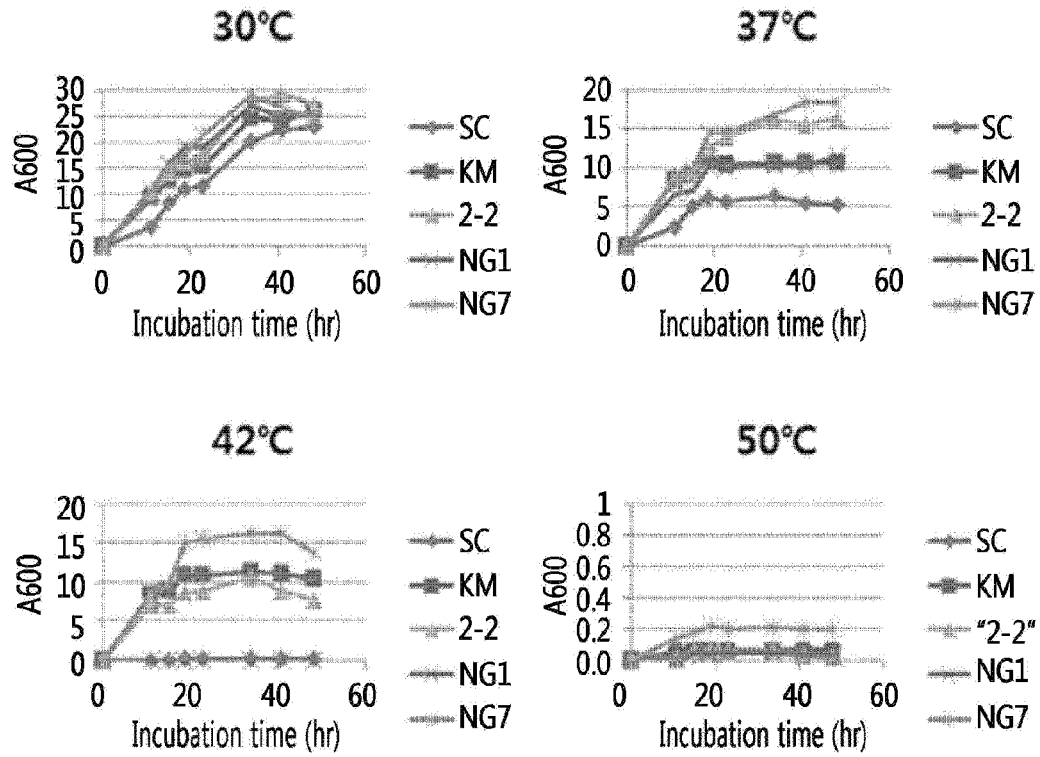
[FIG. 7]
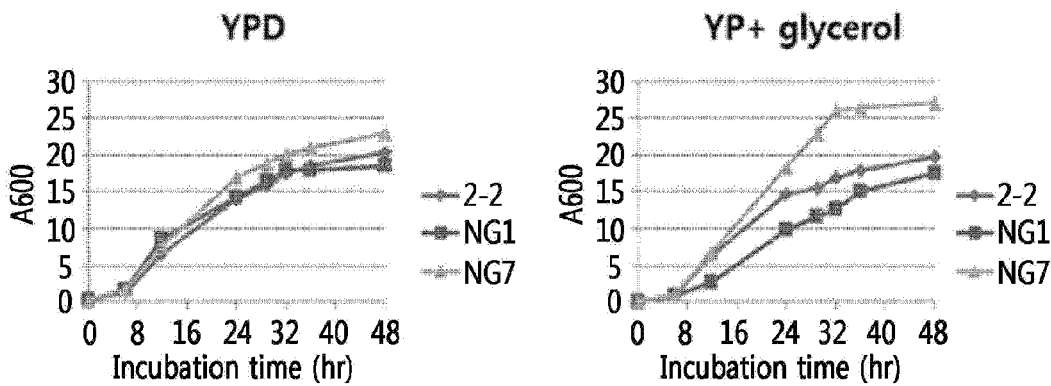

[FIG. 8]
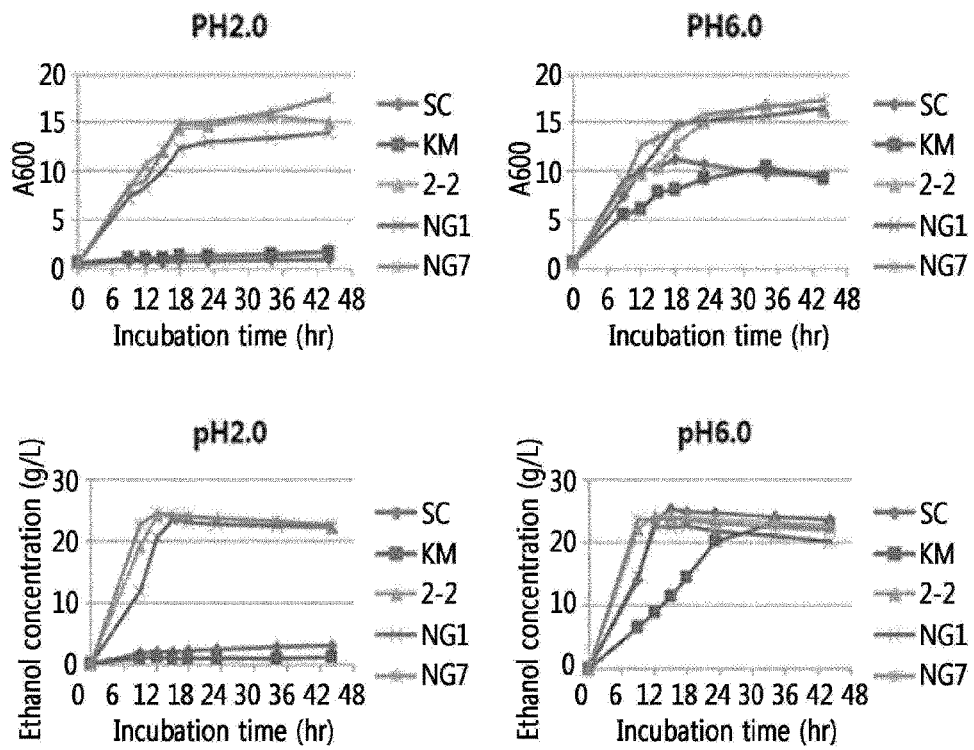

[FIG. 9]
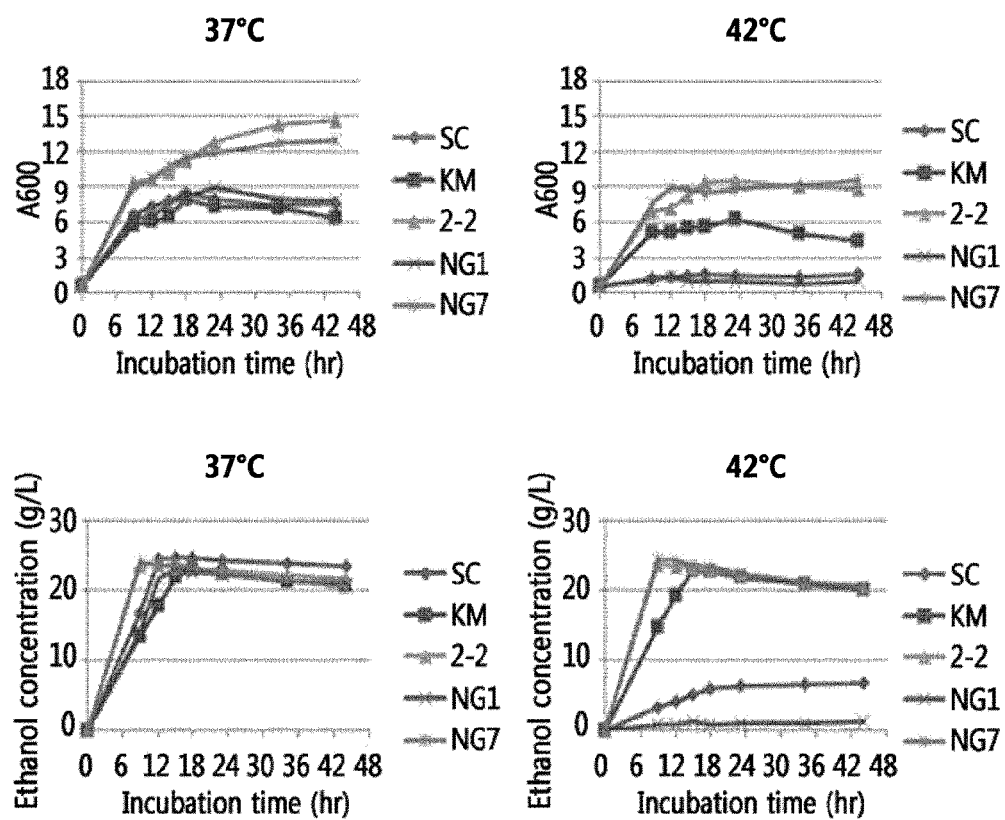

[FIG. 10]
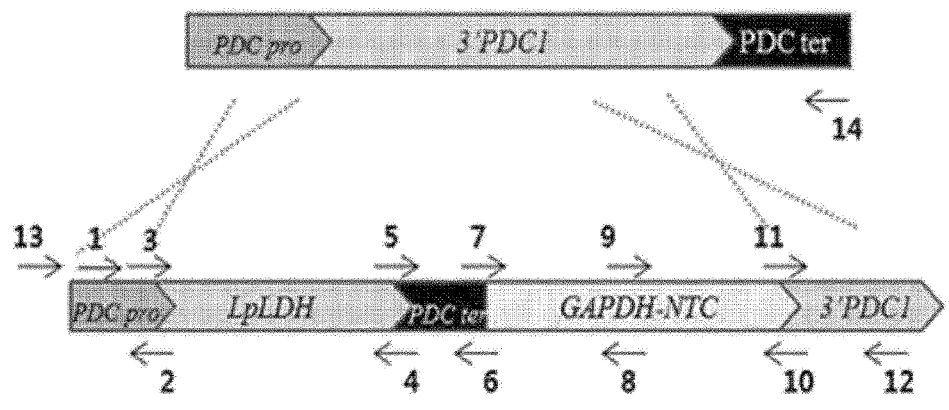
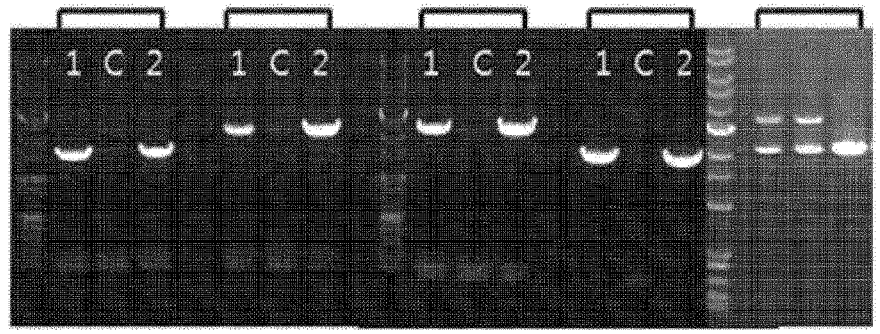

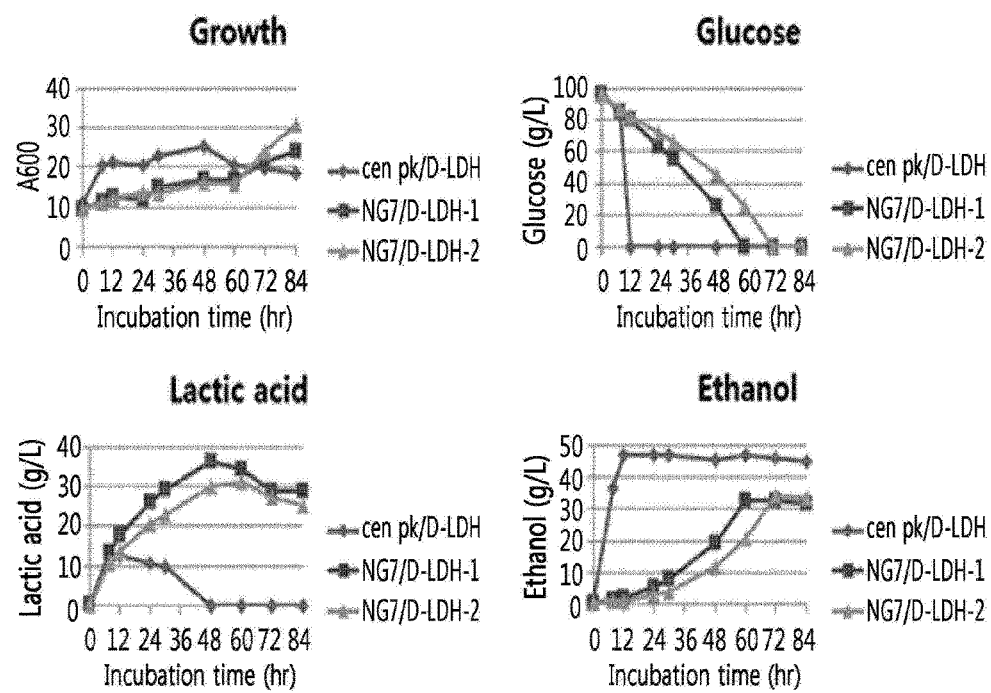
[FIG. 11]

[FIG. 12]
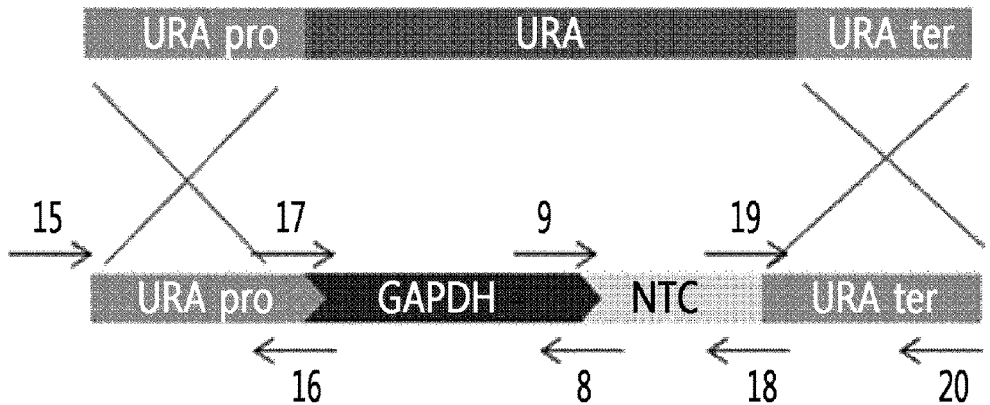
Results of PCR using 15/20 primers
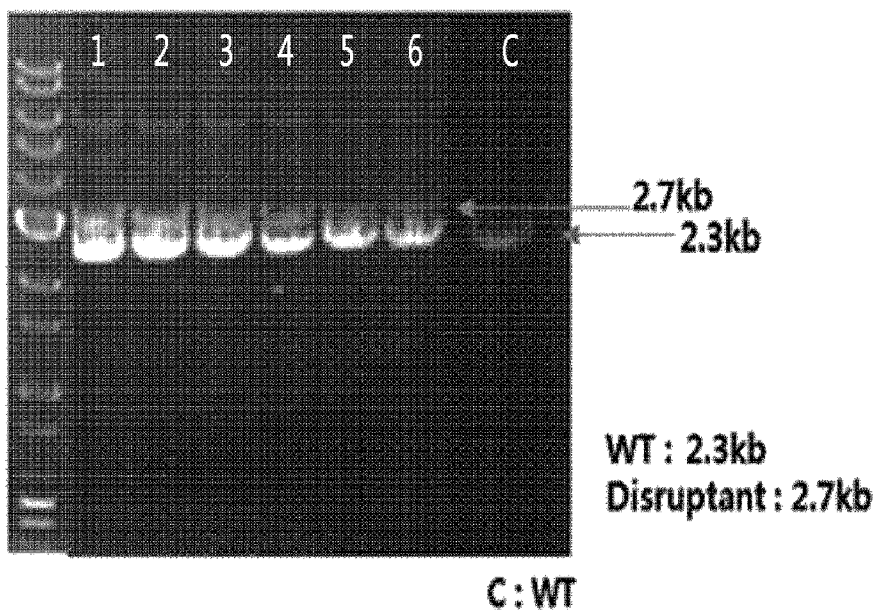
WT : 2.3kb
Disruptant : 2.7kb
C : WT

[FIG. 13]
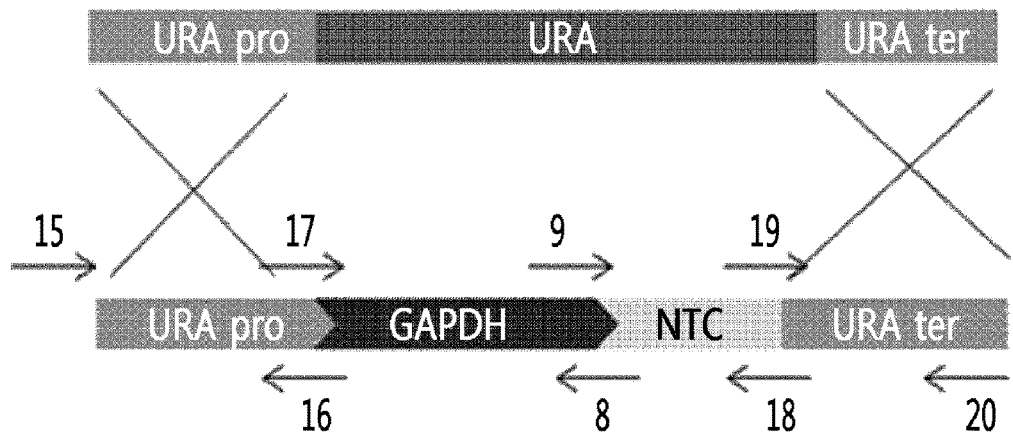
Results of PCR using 15/20 primers
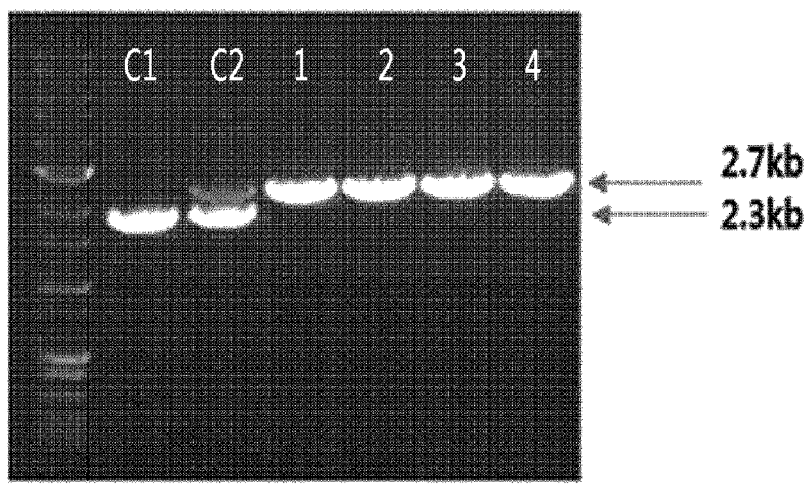
C1 : WT, C2: 1 copy disruptant

[FIG. 14]
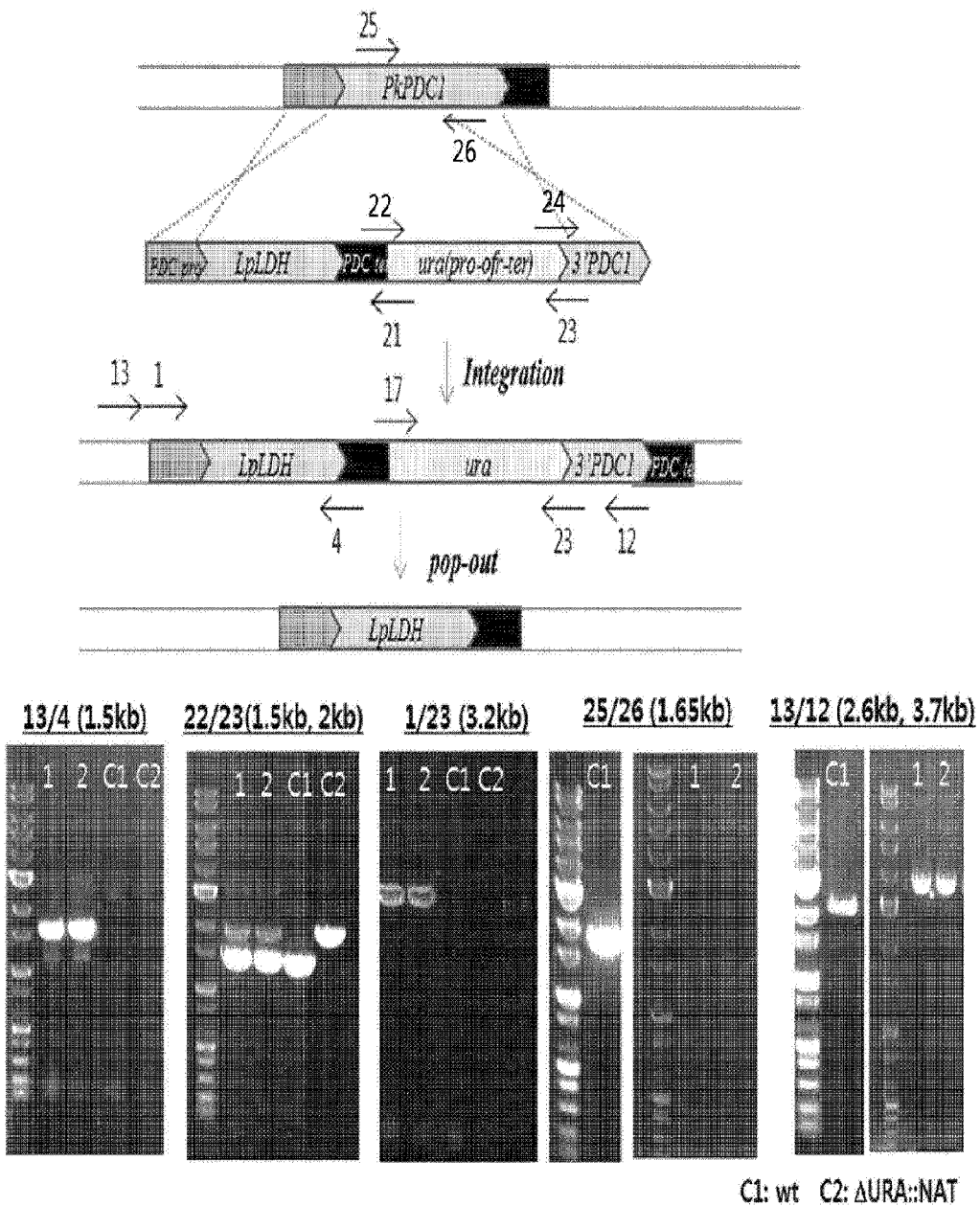

[FIG. 15]
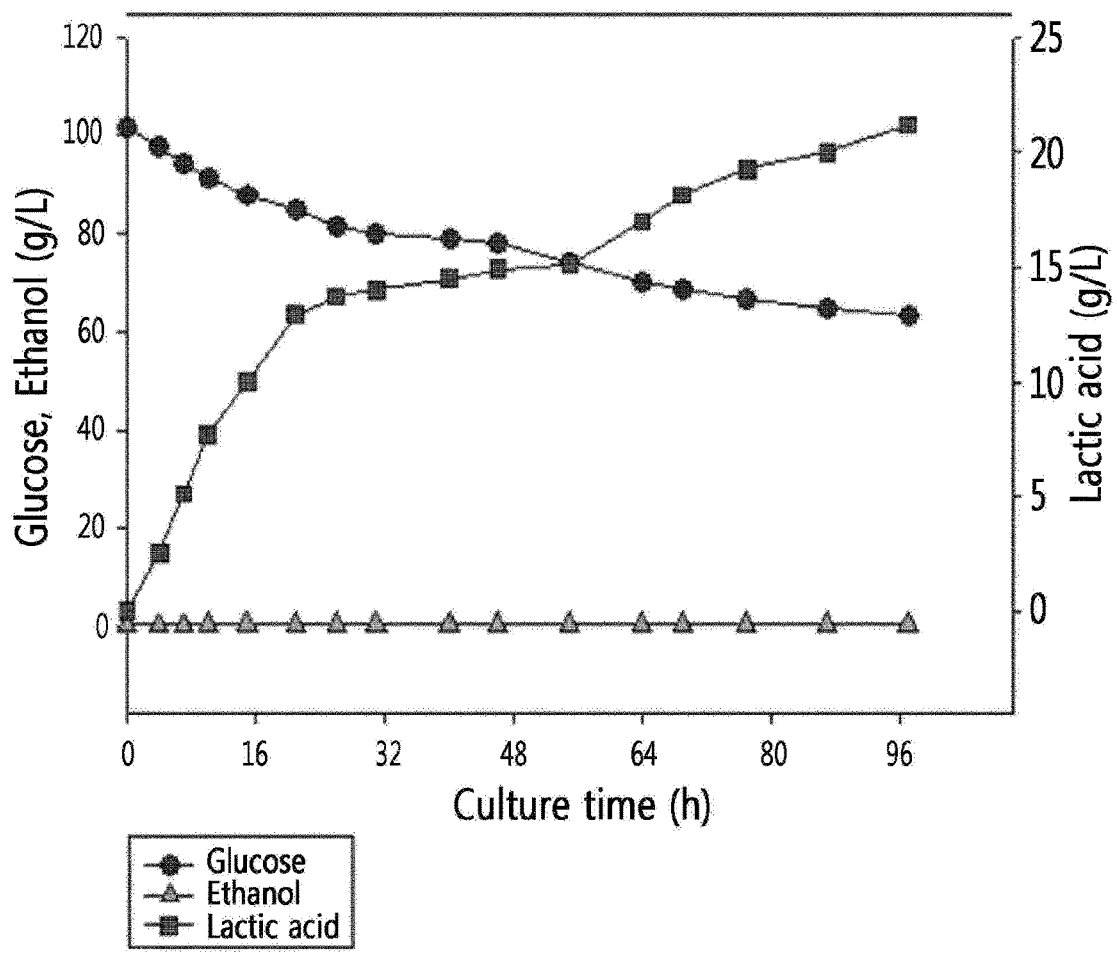
[FIG. 16]
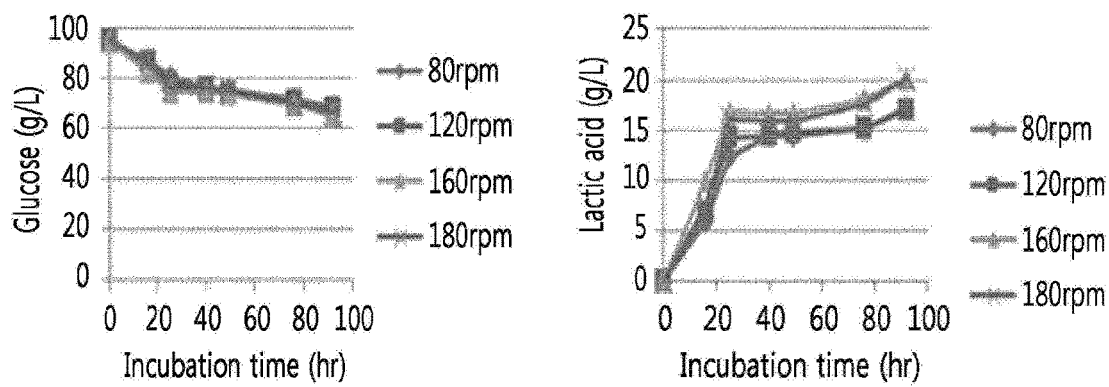

[FIG. 17]
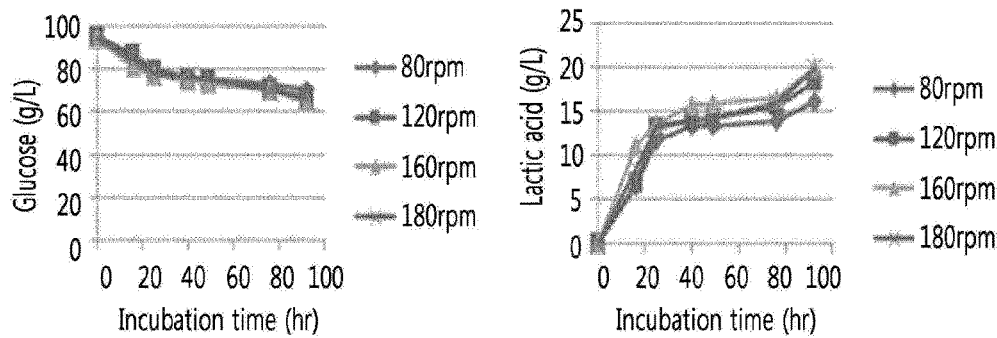
[FIG. 18]
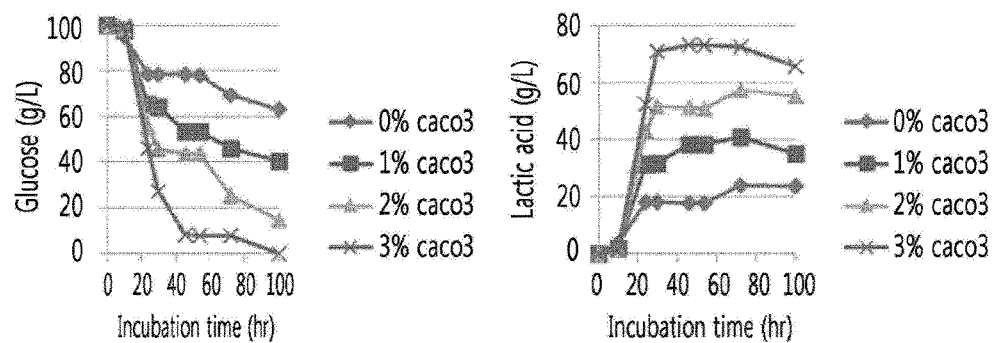

[FIG. 19]
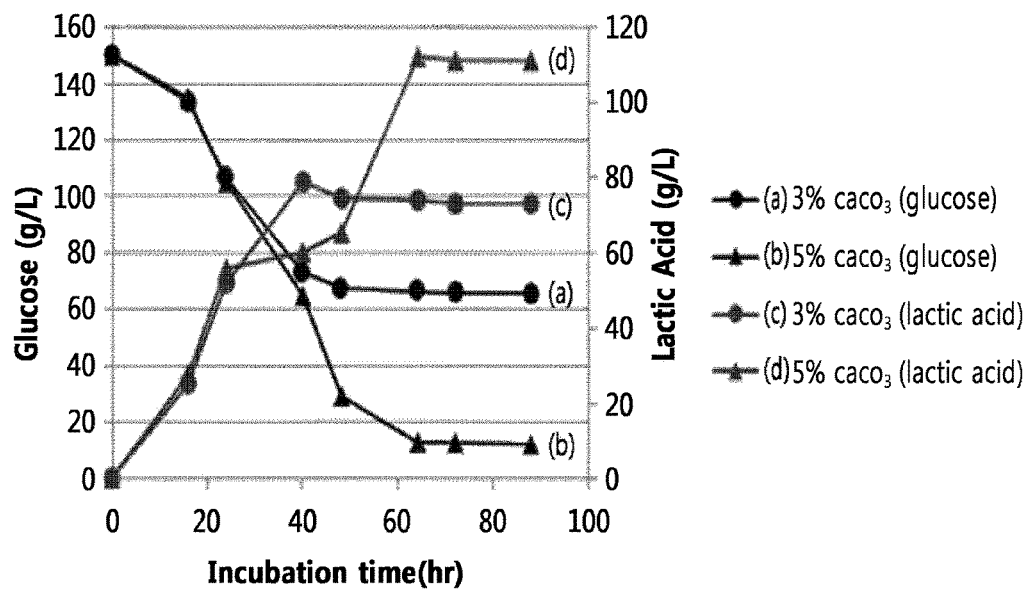

[FIG. 20]
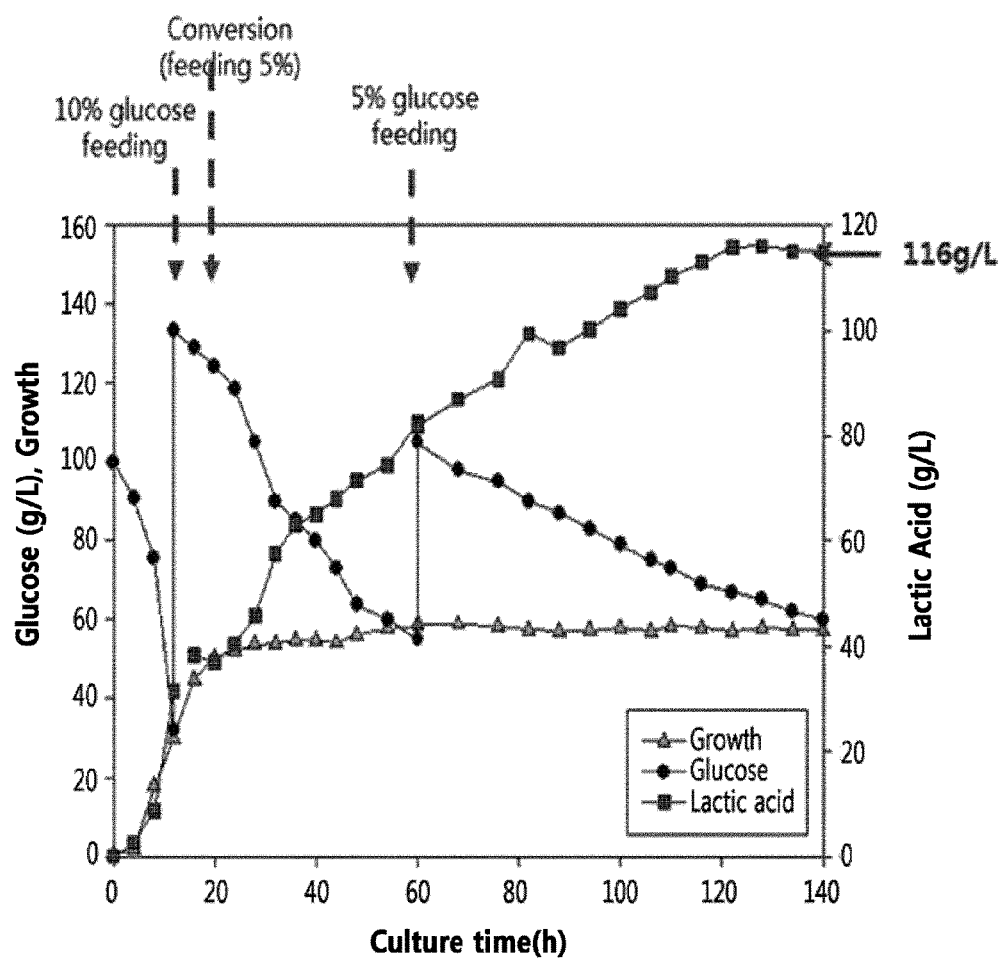

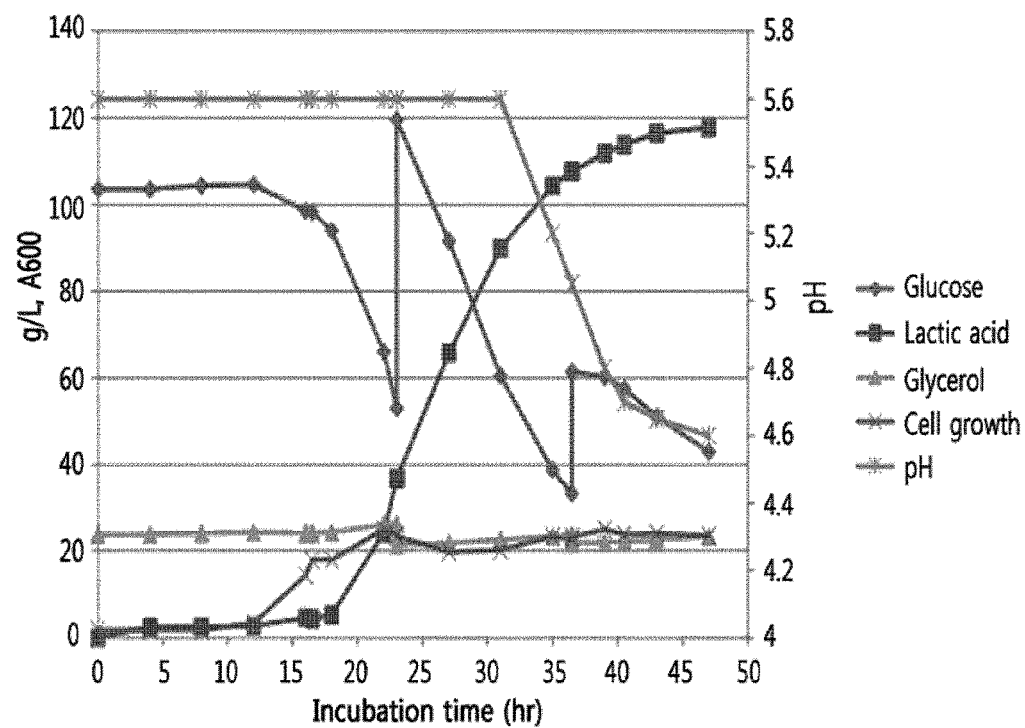
[FIG. 21]

PICHIA KUDRIAVZEVII NG7 MICROORGANISM AND USES THEREOF

RELATED APPLICATIONS

This application is a 35 U.S.C. § 371 filing of International Application No. PCT/KR2015/006314, filed Jun. 22, 2015, which claims priority to Korean Patent Application No. 10-2014-0075461, filed Jun. 20, 2014, each of which are incorporated herein by reference in their entireties.

TECHNICAL FIELD

The present invention relates to a novel *Pichia kudriavzevii* NG7 microorganism having acid resistance and heat resistance, a composition for producing an organic acid or alcohol containing the microorganism or a culture thereof, and a method for producing an organic acid or alcohol including culturing the microorganism.

BACKGROUND ART

Organic acids are widely used in various industrial fields including foods, medicines and pharmaceuticals, cosmetics, etc. Since the first commercialization of lactic acid in 1880, citric acid was commercialized in 1923, and the commercialization of acetic acid, itaconic acid, succinic acid, etc. followed. These organic acids are mostly produced by fermentation or chemical synthesis, and among them, 70 or more organic acids are produced by fermentation and are synthesized via glycolytic and citric acid pathways. Among these organic acids, acetic acid, lactic acid, citric acid, tartaric acid, malic acid, etc. can be produced on a large scale. In particular, in the case of lactic acid, polylactic acid has been confirmed to be a biodegradable polymer that can replace plastics produced from petroleum, and thus there has been a significant increase in the demand for lactic acid used as a monomer.

For the use of lactic acid as a monomer of polylactic acid, it is necessary to selectively produce optical isomers of lactic acid, and in this regard, a method of using a microorganism is preferred to the existing method of chemical synthesis. There are many known Lactobacilli, which are microorganisms producing lactic acid. However, when lactic acid is produced by culturing these microorganisms, there is a disadvantage in that two kinds of optical isomers (D-lactate and L-lactate) are produced together, thus requiring genetic manipulation, and also the microorganisms have a weak acid resistance.

Additionally, the lactic acid accumulated during the fermentation process of lactic acid can acidify the pH of a given medium, thus inhibiting the growth of a given strain. Therefore, a method of adding a neutralizing agent to the medium has been used in the lactic acid fermentation. Calcium carbonate, which is most widely used in the above method, can form a calcium salt by binding to lactic acid, and during the process of recovering lactic acid by treating precipitates with an acid solution after the fermentation process, lime can be formed in the same molar amount as that of lactic acid. The method can complicate the purification process, generate strong acidic waste water, and form by-products, thereby increasing the production cost of lactic acid. To solve these problems, there is a growing interest on the use of acid-resistant microorganisms capable of minimizing the use of a neutralizing agent (*Biotechnolbi Advances*, 2013; 31: 877-902). Although wild-type yeasts cannot produce lactic acid, they have a significantly higher stress resistance than that of bacteria, and thus studies on lactic acid production in yeasts based on this characteristic are competitively conducted. In particular, studies on lactic acid production in an acidic condition without using a neutralizing agent were conducted in various kinds of yeasts by manipulating the ethanol production pathway of an acid-resistant strain to produce lactic acid instead of ethanol (*Biotechnol Genet Eng Rev.* 2010; 27: 229-256).

Additionally, bioethanol, which has a high potential as a green fuel, is utilized as an alternative fuel that can simultaneously solve serious environmental problems such as global warming while reducing dependence on oil energy. However, the rapidly-growing demand for the first generation bioethanol has caused the prices of crop products such as corn and sugarcane to soar, and in addition, has induced the rise of the prices of other crops, and thus the bioethanol production for the resolution of energy issues is becoming a new cause for food problems.

Due to the above problem, the so-called second generation biofuel, cellulosic bioethanol, is spotlighted as a new alternative. Cellulosic bioethanol is ethanol prepared from glucose, which is produced by decomposing cellulose, the most abundant organic material on earth and a major constituting component of plant cell walls. Accordingly, unlike the first generation method of producing ethanol by fermentation of corn starch at present, the method for producing cellulosic bioethanol is a method for producing bioethanol using all tissues such as leaves, stems, roots, etc. of corn, which have been discarded or burnt. By the above method, bioethanol can be produced from the tissues of all plants such as corn husk, rice bran, grass, reeds, flame grass, wood waste, etc.

The materials serving as raw materials for the second generation biofuel are called lignocellulosic biomass, and lignocellulosic biomass largely consists of three components: cellulose, hemicelluloses, and lignin. Among these, hemicelluloses contain arabinose and xylose in an amount of about 5% to about 20%. The production of bioethanol using pentose sugars, which constitute a significant part of hemicelluloses, is currently performed with many limitations.

Additionally, research on biodiesel, which is an environmentally friendly clean alternative energy, has been actively conducted. However, biodiesel has a disadvantage in that it produces glycerol as a by-product. Glycerol can be used as a raw material for cosmetics, food preparations, and petrochemical derivatives but it has a disadvantage in that there is a limitation on host cells that can utilize it as a raw material for sugar.

DISCLOSURE

Technical Problem

The present inventors have made efforts to provide a yeast microorganism which can produce useful products using various raw materials for sugar while having heat resistance and acid resistance. As a result, they have succeeded in isolating and identifying the *Pichia kudriavzevii* NG7 microorganism, which is a yeast microorganism having excellent heat resistance and acid resistance, and confirmed that the microorganism can produce organic acids and alcohol by genetic manipulation, thereby completing the present invention.

Technical Solution

An object of the present invention is to provide a novel *Pichia kudriavzevii* NG7 microorganism having acid resistance and heat resistance.

Another object of the present invention is to provide a composition for producing an organic acid or alcohol including the microorganism or a culture thereof.

A further object of the present invention is to provide a method for producing an organic acid or alcohol including culturing the microorganism.

Advantageous Effects of the Invention

The novel *Pichia kudriavzevii* NG7 strain of the present invention exhibits excellent heat resistance and acid resistance. Therefore, with respect to lactic acid production, the microorganism enables efficient production of lactic acid in a condition without using a neutralizing agent or a condition minimizing the use of the neutralizing agent.

BRIEF DESCRIPTION OF DRAWINGS

FIG. 1 shows the growth curves of yeasts isolated from grape skin according to pH.

FIG. 2 shows the growth curves of yeasts isolated from peach skin according to pH.

FIG. 3 shows the growth curves of yeasts isolated from palm sludge according to pH.

FIG. 4 shows the growth curves of yeasts isolated from palm sludge compost according to pH.

FIG. 5 shows the growth curves of yeasts in YPD liquid media containing 0%, 4%, 5%, and 6% lactic acid, respectively.

FIG. 6 shows the growth curves of yeasts according to the culture temperature by culturing at 30° C., 37° C., 42° C., and 50° C., respectively.

FIG. 7 shows growth curves of novel yeast microorganisms, i.e., 2-2, NG1, and NG7 microorganisms, in glycerol-containing medium.

FIG. 8 shows the graphs comparing the cell growth and ethanol productivity of the novel yeast microorganisms (i.e., 2-2, NG1, and NG7 microorganisms), *Saccharomyces cerevisiae* (SC), and *Kluyveromyces marxianus* (KM), according to pH.

FIG. 9 shows the graphs comparing the cell growth and ethanol productivity of the novel yeast microorganisms (i.e., 2-2, NG1, and NG7 microorganisms), *Saccharomyces cerevisiae* (SC), and *Kluyveromyces marxianus* (KM), according to culture temperature.

FIG. 10 shows a schematic diagram for the deletion of PDC1 gene and insertion of a gene for D-type lactic acid-producing enzyme in NG7 and the results confirming the deletion and introduction of the genes by PCR.

FIG. 11 shows the graphs comparing the growth curves, glucose consumption, lactic acid productivity, and ethanol productivity of a transformed NG7 microorganism (i.e., NG7/D-LDH-1 and -2), in which one copy of the PDC1 gene was deleted and the LDH gene was introduced and a *Saccharomyces cerevisiae* microorganism (i.e., CEN.PK/D-LDH), in which the same gene was deleted and LDH gene was introduced as in the transformed NG7.

FIG. 12 shows a schematic diagram for the inactivation of one copy of URA3 gene of NG7 and the PCR results confirming the introduction of a gene of the transformant.

FIG. 13 shows a schematic diagram for the inactivation of the second URA3 gene of NG7 microorganism and the PCR results confirming the deletion of a gene of the transformant.

FIG. 14 shows the results confirmed by PCR using primers corresponding to each number after inserting the D-LDH gene into the position of the PDC1 gene using the URA3 selection marker.

FIG. 15 shows the graphs confirming the consumed glucose, lactic acid and ethanol produced by NG7Δpdc1/D-LDH microorganism, in which both of the PDC1 genes are deleted, by culturing them without neutralizing agents.

FIG. 16 shows the graphs confirming the effect of rpm in an incubator on lactic acid production of the NG7Δpdc1/D-LDH microorganism during its cultivation, in which both of the PDC1 genes are deleted.

FIG. 17 shows the graphs confirming the effect of rpm in an incubator on lactic acid production when the initial inoculum volume of the NG7Δpdc1/D-LDH microorganism was increased.

FIG. 18 shows the graphs confirming lactic acid production of the NG7Δpdc1/D-LDH microorganism during its cultivation while adding a pH-neutralizing agent ($CaCO_3$) in a concentration of 0% to 3%.

FIG. 19 shows the graphs confirming the amount of consumed glucose and the amount of produced lactic acid by the NG7Δpdc1/D-LDH microorganism during its cultivation while adding a pH-neutralizing agent ($CaCO_3$) thereto in a concentration of 3% and 5%.

FIG. 20 shows the graphs confirming the amount of consumed glucose and the amount of produced lactic acid by the NG7Δpdc1/D-LDH microorganism during its cultivation via fed-batch culture in a pH-controlled condition.

FIG. 21 shows the graphs confirming the amount of consumed glucose and the amount of produced lactic acid by the NG7Δpdc1/D-LDH microorganism during its cultivation via fed-batch culture in a condition using the minimal amount of a neutralizing agent.

BEST MODE

To achieve the above objects, an exemplary embodiment relates to a novel *Pichia kudriavzevii* NG7 microorganism which exhibits heat resistance and acid resistance, and specifically, the microorganism of the present invention may be the microorganism deposited under the Accession Number KCTC12840BP.

As used herein, the term "*Pichia kudriavzevii* microorganism" refers to a kind of yeasts belonging to *Ascomycetes* and the microorganism forms various pseudohyphae. Many strains belonging to the genus *Pichia* are reported and they can exhibit a wide variety of physiological characteristics depending on the strain. In some cases reported, different research groups showed different results even for the same strain. Accordingly, in the present invention, it is an important process to select a particular *Pichia kudriavzevii* strains having the required characteristics.

The *Pichia kudriavzevii* NG7 microorganism of the present invention is a microorganism isolated from grape skin, and it was confirmed by a feature analysis that the microorganism has excellent heat resistance and acid resistance and thus can grow at 42° C. and pH 2. The nucleotide sequence of the microorganism was analyzed, and as a result, the microorganism was shown to have a homology of 98.7% with that of *Pichia kudriavzevii*, and thus the microorganism was named as "*Pichia kudriavzevii* NG7", and the nucleotide sequences of ITS1, 5.8S rRNA, ITS2, and 28S rRNA thereof were registered with the GenBank of NCBI under the registration number KM016456. Additionally, the microorganism was deposited with the Korean Collection for Type Cultures (KCTC) on Jun. 17, 2014, with the accession number KCCM18297P. The deposition of the microorganism was converted into an international deposition under the Budapest Treaty on Jun. 9, 2015 based on the Korean deposition, and assigned the Accession Number of KCTC12840BP.

Specifically, the *Pichia kudriavzevii* NG7 microorganism of the present invention may be a microorganism in which an activity of orotidine 5'-phosphate decarboxylase (URA3) is inactivated, and any microorganism in which the activity of orotidine 5'-phosphate decarboxylase in the *Pichia kudriavzevii* NG7 as a parent microorganism is inactivated to inhibit uracil synthesis may be included without limitation.

As used herein, the term "orotidine 5'-phosphate decarboxylase (URA3)" refers to an enzyme which is involved in the biosynthesis of pyrimidine ribonucleotides. The microorganism in which URA3 gene is deleted is a uracil auxotrophic microorganism. Since URA3 gene can be used as an auxotrophic selection marker gene, in an embodiment of the present invention, a microorganism in which orotidine 5'-phosphate decarboxylase of *Pichia kudriavzevii* NG7 is deleted was prepared (Example 10). Such a microorganism enables an easy selection of the introduction or deletion of a gene using URA3 gene.

Additionally, more specifically, the *Pichia kudriavzevii* NG7 microorganism of the present invention may be a microorganism in which an activity of pyruvate decarboxylase is further inactivated, but any microorganism in which the activity of pyruvate decarboxylase is inactivated from a parent microorganism, *Pichia kudriavzevii* NG7, and thereby alcohol production is inhibited may be included without limitation.

As used herein, the term "pyruvate decarboxylase (PDC1)" refers to an enzyme which catalyzes a reaction to produce carbonic acid and acetaldehyde by acting on pyruvate ($CH_3COCOOH \rightarrow CH_3CHO + CO_2$). With respect to alcohol production, it is an essential enzyme in a step of alcohol fermentation. Accordingly, the present invention can provide a microorganism in which the pyruvate decarboxylase present in the above microorganism is inactivated and thereby alcohol production by fermentation is inhibited.

Specifically, the microorganism may be a microorganism of which the ethanol production is decreased if cultured in sugar-containing medium, compared to the microorganism in which pyruvate decarboxylase is not inactivated. Additionally, the inactivation of pyruvate decarboxylase is achieved by substitution, deletion, or addition in the gene for the corresponding enzyme. The pyruvate decarboxylase may be expressed by a gene consisting of SEQ ID NO: 20, but the gene is not limited thereto.

Generally, gene inactivation in a microorganism can be performed in various forms. For example, gene expression can be reduced by modification of the signaling structure for gene expression or antisense-RNA techniques. Examples of the signaling structures for gene expression may include a repressor gene, an activator gene, an operator, a promoter, an attenuator, a ribosome-binding site, an initiation codon, and a terminator, but are not limited thereto.

Additionally, an RNA interference (RNAi) method, which employs a mechanism that inhibits the expression of a target gene by inducing the decomposition of the mRNA of the target gene via introduction of a double stranded RNA (dsRNA) which consists of a sense strand having a homologous sequence to the mRNA of the target gene, and an antisense strand having a complementary sequence of the mRNA of the target gene may be used. As an alternative, gene inactivation may be performed by blocking the function of a target gene by inducing a mutation mediated by a transposon, which is a DNA sequence capable of moving to a different position within the genome of a single cell. The mutations that can induce a change, increase or decrease of catalytic activity of a protein are well known in the art (Qiu & Goodman, *Journal of Biological Chemistry* 272: 8611-8617, 1997).

Specifically, gene inactivation may be performed using any method selected from modification of a single or complex nucleotide sequence, deletion of a single or complex nucleotide sequence, insertion of an exogenous gene within a gene, deletion of the entire gene group, insertion of an inhibitory sequence of a promoter of a gene group, a mutation of a promoter, insertion of an inhibitory control sequence of expression of a gene group, introduction of RNAi with respect to a single or complex nucleotide sequence in a gene group, a transposon-mediated mutation, and a combination of the variants thereof.

The methods described above can generally be understood by one of ordinary skill in the art and may be performed as described in Sambrook et al. (*Molecular Cloning*: A Laboratory Manual, Third Edition, Cold Spring Harbor Press 2001).

The methods may be a method to significantly reduce the activity of a protein expressed from a gene by modifying a single or complex nucleotide sequence at the active site of the nucleotide sequence of the gene; or a method to prevent the complete expression of a protein by deletion of a single or complex gene, or by insertion of an exogenous gene such as antibiotic-resistant gene or another gene within the nucleotide sequence. Specifically, a method to delete the entire nucleotide sequence of a gene present in the chromosome may be used. Alternatively, gene inactivation may be performed by a combination of variants of the above methods.

Additionally, an object of the present invention is to provide a microorganism which has the characteristics of producing an organic acid or alcohol. For this purpose, an organic acid and alcohol may be simultaneously produced using a microorganism in which one of the two copies of the PDC1 gene in the novel *Pichia kudriavzevii* NG7 microorganism is deleted and an exogenous gene associated with the production of the organic acid is introduced.

In an exemplary embodiment of the present invention, it was confirmed that the microorganism in which one copy of the PDC1 gene is deleted and the lactate dehydrogenase (LDH) gene is introduced produces lactic acid and ethanol (Example 9).

Additionally, an object of the present invention is to provide a microorganism which has the characteristics of producing only an organic acid at high concentration while minimizing ethanol production. For this purpose, an organic acid may be produced using a microorganism in which both the two copies of the PDC1 gene in the novel *Pichia kudriavzevii* NG7 microorganism are deleted and an exogenous gene associated with the production of the organic acid is introduced.

In an exemplary embodiment of the present invention, it was confirmed that the microorganism in which the two copies of the PDC1 gene are deleted and the LDH gene is introduced produces lactic acid while not producing ethanol (Example 12).

The microorganism of the present invention may be a *Pichia kudriavzevii* NG7 microorganism in which an activity of PDC1 is inactivated and an activity of lactate dehydrogenase is further introduced, and specifically a microorganism which was deposited under the Accession Number KCTC12841BP and KCTC12842BP. However, for the purpose of the present invention, an exogenous gene(s) such as a gene(s) encoding the enzyme(s) and factor(s) other than lactate dehydrogenase involved in the production of an organic acid may be introduced into the *Pichia kudriavzevii* NG7 microorganism, and a different kind of an organic acid may be produced according to the kind of the gene being introduced.

As used herein, the term "exogenous gene" refers to a gene in a case when a nucleic acid sequence which originally did not present in a given wild-type microorganism was introduced into the microorganism from the outside for a particular purpose. In particular, in the present invention, exogenous gene refers to a gene associated with the production of a particular organic acid, and the organic acid may be lactic acid.

Specifically, the target organic acid of the microorganism of the present invention may be an L-type or D-type optical isomer, and in particular, L-lactic acid or D-lactic acid, but is not limited thereto, and the organic acid may be produced by introducing a necessary gene depending on the type of the optical isomer of the organic acid to be produced.

Specifically, the exogenous gene which is introduced into a microorganism for the production of lactic acid as one of organic acids, may be a gene having an activity of lactate dehydrogenase (LDH). As used herein, the term "lactate dehydrogenase" generally refers to an enzyme which converts L-lactic acid or D-lactic acid to pyruvate by dehydrogenation using $NAD^+$, and in the case of catalyzing the final step of glycolysis, which is the reverse reaction thereof, the enzyme produces L-lactic acid or D-lactic acid by reducing pyruvate using NADH. That is, the lactate dehydrogenase of the present invention may be an L-lactate dehydrogenase or D-lactate dehydrogenase, and specifically, a D-lactate dehydrogenase.

The gene having an activity of the lactate dehydrogenase may include not only the gene encoding native lactate dehydrogenase but also a gene(s) for the enzyme with the equivalent activity having a homology of at least 75%, 80%, 85%, 90%, 95%, 96%, 97%, 98%, or 99% to the sequence thereof. Additionally, those genes in which a mutation is induced on the native lactate dehydrogenase may be included regardless of their sequences as long as they have an activity of the lactate dehydrogenase.

Information on the lactate dehydrogenase may be confirmed in a known database such as the GenBank of NCBI, and the gene may consist of the nucleotide sequence of SEQ ID NO: 19, but is not limited thereto.

Specifically, the microorganism of the present invention may be one in which an activity of pyruvate decarboxylase is weakened compared to its endogenous activity and an activity of lactate dehydrogenase is further introduced. The weakening of the endogenous activity may be performed by inactivating one of the two copies of the pyruvate decarboxylase gene present in the wild-type microorganism, and furthermore, the weakening may be performed by substituting one of the pyruvate decarboxylase genes with a gene encoding lactate dehydrogenase. More specifically, the microorganism of the present invention may be the microorganism deposited under the Accession No. KCTC12841BP, but is not limited thereto.

Additionally, specifically, the microorganism of the present invention may be one in which an activity of pyruvate decarboxylase is inactivated and an activity of lactate dehydrogenase is further introduced. The activity of the pyruvate decarboxylase in the microorganism of the present invention may be inactivated by inactivating both of the two copies of the pyruvate decarboxylase gene present in the wild-type microorganism, and furthermore, the activity may be inactivated by substituting the pyruvate decarboxylase gene with a gene encoding lactate dehydrogenase. More specifically, the microorganism of the present invention may be the microorganism deposited under the Accession No. KCTC12842BP, but is not limited thereto.

The weakening of the activity of the pyruvate decarboxylase means that the activity of the pyruvate decarboxylase is decreased compared to that of an unmodified microorganism and it may also include a case in which the activity of the pyruvate decarboxylase is removed. The weakening of the pyruvate decarboxylase activity may be performed by applying various methods well-known in the art.

Examples of the methods may include a method for replacing the gene encoding the enzyme on the chromosome with a gene mutated to reduce the activity of the enzyme, including the case when the activity of the enzyme is removed; a method of introducing a mutation in the expression control sequence of the gene encoding the enzyme on the chromosome; a method of replacing the expression control sequence of the gene encoding the enzyme with a sequence having a weaker activity; a method of deleting the gene encoding the enzyme on the chromosome; a method of introducing an antisense oligonucleotide capable of inhibiting the translation of the mRNA into a protein by complementarily binding to a transcript of the gene on the chromosome; etc., but the methods are not limited thereto. The methods described above may be applied in the same manner for weakening the activities of other enzymes. In the present invention, the methods may include a method to replace the gene encoding pyruvate decarboxylase on the chromosome, but are not limited thereto.

Additionally, in another exemplary embodiment, the present invention relates to a composition for producing an organic acid or alcohol, including the microorganism or a culture thereof. Specifically, the microorganism can use glycerol as a carbon source.

The microorganism is the same as explained above.

As used herein, the term "culture" refers to a medium which includes a cultured microorganism, a metabolite thereof, and extra nutrients, etc., which are obtained by culturing the *Pichia kudriavzevii* NG7 microorganism of the present invention in medium capable of supplying nutrients to enable growth and survival of the microorganism in vitro for a particular period of time, but it also includes a culture broth in which the microorganism is removed after culturing the microorganism. The *Pichia kudriavzevii* NG7 microorganism may exhibit the capability of producing organic acid and alcohol, and specifically, the capability of producing lactic acid and alcohol, and thus the microorganism or a culture thereof may be used as a composition for producing an organic acid or alcohol. Specifically, the organic acid may be lactic acid and the alcohol may be ethanol.

Recently, the second generation bioethanol capable of fermenting polysaccharides into ethanol is highlighted, and the second generation bioethanol requires a glycosylation process that glycosylates polysaccharides into mono- or disaccharides that can be fermented into ethanol. Such a glycosylation process may be performed using an enzyme or acid.

The glycosylation of an enzyme is a process of decomposing the carbohydrates of biomass into monosaccharides using a cellulolytic enzyme such as cellulase. The enzyme itself is a biological catalyst and has advantages in that it has a relatively low reaction temperature, is environmentally friendly due to little waste production, and requires a low energy. However, the enzyme has disadvantages in that it is expensive and requires a long reaction time. Additionally, the enzyme has a disadvantage in that the enzyme activity can be limited by various factors.

Meanwhile, acid glycosylation is a process of decomposing the carbohydrates of biomass via hydrolysis into monosaccharides using an acid at high temperature, and an inexpensive acid such as sulfuric acid is mainly used. Accordingly, acid glycosylation has advantages in that the process has a short reaction time and requires a low cost. However, the process has disadvantages in that the process uses an acid and thus a neutralization step is required and wastes (precipitants) are produced during the neutralization process, a glycolytic product is produced in an acidic and high-temperature condition and the glycolytic product may act as an inhibitory factor to the following fermentation process, and a further progress of decomposition may produce unwanted by-products such as formic acid, formaldehyde, etc.

Accordingly, the glycosylation using an enzyme is acknowledged as a preferred process and is thus widely studied. The reaction conditions for the glycosylation using an enzyme are relatively mild and thus an integrated single biological process simultaneously performing glycosylation and fermentation processes in a reactor may be enabled. When the integrated single biological process is performed, fermentable monosaccharides, etc. are consumed by fermentation as soon as they are produced. Therefore, the disadvantage that the reaction is terminated due to the increased concentrations of monosaccharides, etc. (i.e., the products accumulated during the enzyme glycosylation) when glycosylation and fermentation are performed separately can be resolved spontaneously. Furthermore, the integrated single biological process has an advantage in that high glycosylation efficiency can be obtained with a small amount of an enzyme because the enzyme glycosylation process proceeds continuously, and is thus capable of reducing the cost. However, although the reaction conditions for the enzyme glycosylation are mild, it is necessary to maintain the internal temperature of a reactor at a relatively high temperature (about 40° C.) for exhibiting the optimal activity of the enzyme. Accordingly, for the production of the second generation bioethanol by the integrated single biological process, it is essential to develop a microorganism which can stably grow at high temperature while simultaneously having ethanol productivity.

In an exemplary embodiment of the present invention, it was confirmed that the NG7 microorganism can grow at pH 2.0 and produce lactic acid and ethanol, thus having an excellent acid resistance (FIG. 8). Additionally, the growth curves and the production amounts of lactic acid and ethanol were measured according to temperature, and as a result, it was confirmed that the microorganism can grow at a high temperature of 42° C., and lactic acid and ethanol are actively produced (FIG. 9).

From the above, it was confirmed that the novel *Pichia kudriavzevii* NG7 microorganism of the present invention not only exhibits excellent acid resistance and heat resistance but also has excellent productivity of lactic acid and ethanol, and thus the microorganism has high industrial applicability (FIG. 11).

The microorganism of the present invention can grow using the saccharides and glycerol which are generally-known carbon sources, but also crude glycerol generated during biodiesel production as a carbon source, and the microorganism can produce an organic acid and/or alcohol using the same.

Additionally, in an exemplary embodiment of the present invention, the NG7 microorganism showed excellent growth even when using glycerol generated during biodiesel production as a carbon source (FIG. 7).

As used herein, the term "crude glycerol" refers to a biofuel, or specifically one that is produced as a by-product during biodiesel production, and about 10 kg of crude glycerol is produced per 100 kg of biodiesel production. The crude glycerol includes impurities such as fatty acid salts (soaps), various salts including peroxides (K, Na, or Cl), methanol, etc., in addition to glycerol, but is not limited thereto.

Furthermore, in an exemplary embodiment of the present invention, the activity of lactate dehydrogenase of the microorganism of the present invention was measured, and as shown in Table 9, it was confirmed that the activity of lactate dehydrogenase of the *Pichia kudriavzevii* NG7 microorganism is significantly higher than that of the positive control group.

In an exemplary embodiment, the present invention relates to a method for producing an organic acid or alcohol including culturing the microorganism.

Specifically, the method for producing an organic acid or alcohol of the present invention may include culturing a transformed microorganism in which the alcohol production pathway is partially blocked by deleting one copy of the two copies of the gene in the microorganism involved in the production of alcohols and the organic acid and alcohol productivities are maintained at high levels while maintaining the growth ability.

Additionally, the method for producing an organic acid of the present invention may include culturing a transformed microorganism in which the alcohol production pathway is completely blocked by deleting both the two copies of the gene in the microorganism involved in the production of alcohols and the organic acid productivity is maintained at high level while maintaining the growth ability.

Specifically, the organic acid may be lactic acid, the alcohol may be ethanol, and the gene involved in the production of alcohols may be a gene encoding pyruvate decarboxylase (PDC1).

Generally, the yeast in which the alcohol production pathway is completely blocked by deleting both copies of the PDC1 gene undergoes a significant decrease in its growth ability, and is thus not suitable for the production of an organic acid. However, it was confirmed that the microorganism of the present invention can be effectively applicable for the production of an organic acid even when the alcohol production pathway is completely blocked (Example 12).

In the present invention, the microorganism may be cultured according to a widely-known method and the culture conditions such as temperature, time, pH of medium, etc. may be appropriately adjusted. Examples of the appropriate culture methods may include fed-batch culture, batch culture, and continuous culture, and specifically batch culture, but are not limited thereto.

Specifically, the method for producing an organic acid or alcohol of the present invention may be performed in a condition where a neutralizing agent is not added.

In an exemplary embodiment of the present invention, it was confirmed that the microorganism of the present invention produced lactic acid while exhibiting a high LDH activity even in a condition where the pH was not adjusted (Examples 12 and 13).

In another exemplary embodiment of the present invention, it was confirmed that the microorganism can produce lactic acid by fed-batch culture in a condition where a neutralizing agent is used in a minimal amount (Example 17).

The medium used in the culture must appropriately meet the requirements of specific strains. Culture media for various microorganisms are disclosed (e.g., Manual of Methods for General Bacteriology. *American Society for Bacteriology*. Washington D.C., USA, 1981). As a carbon source to be used in the medium, sugars and carbohydrates (e.g., glucose, sucrose, lactose, fructose, maltose, molasses, starch, and cellulose); oils and fats (e.g., soybean oil, sunflower oil, peanut oil, and coconut oil); fatty acids (e.g., palmitic acid, stearic acid, and linoleic acid; alcohols (e.g., glycerol and ethanol); and organic acids (e.g., acetic acid, etc.) may be used.

In the present invention, the microorganism may be cultured in medium in which glucose and/or glycerol is contained as a nutrient source(s); may be cultured using various biomass-derived glucide which can be supplied on a large scale at a low price as a nutrient source; and crude glycerol, which is a by-product produced during biodiesel production, may be used as a nutrient source.

Specifically, the method for producing an organic acid or alcohol of the present invention may be one for culturing the microorganism in glycerol-containing medium, and in an exemplary embodiment, it was confirmed that the amount of glycerol, the amount of glucose consumption, and the amount of lactic acid production were proportionate to each other (Example 15). In particular, it was confirmed that when glucose and glycerol were added together the amount of glucose consumption was increased and the amount of lactic acid production was significantly increased by about 40%, compared to when glucose was included alone.

These substances that constitute the medium may be used individually or as a mixture. As a nitrogen source, nitrogen-containing organic compounds (e.g., peptone, yeast extract, meat gravy, malt extract, corn steep liquor, soybean meal powder, and urea) or inorganic compounds (e.g., ammonium sulfate, ammonium chloride, ammonium phosphate, ammonium carbonate, and ammonium nitrate) may be used, and these substances may also be used individually or as a mixture. As a phosphorus source, potassium dihydrogen phosphate or dipotassium hydrogen phosphate or a corresponding sodium-containing salt may be used. Additionally, the culture medium may include a metal salt (e.g., magnesium sulfate or iron sulfate) which is essential for growth, and finally, essential growth-promoting substances such as amino acids and vitamins may be used in addition to the above-mentioned substances. An appropriate precursor may be further added to the culture medium. The above materials to be supplied may be added into the culture at once or appropriately during the cultivation.

DETAILED DESCRIPTION OF THE INVENTION

Hereinafter, the present invention will be described in more detail with reference to the following Examples. However, these Examples are for illustrative purposes only, and the invention is not intended to be limited by these Examples.

Example 1. Isolation of Novel Yeasts with Acid Resistance

For the identification of novel yeasts with acid resistance, various samples (soils within the territory of the Korean Research Institute of Bioscience and Biotechnology (KRIBB) in Daejeon, grape skins, peach skins, palm by-products, and palm by-product compost, etc.) were collected. The collected sample (10 g) was added into sterile distilled water (40 mL) and mixed by vortexing for an hour. Then, the supernatant was diluted stepwise and plated on a solid medium containing antibiotic for inhibition of bacterial growth, YMPS (yeast extract (0.3%), malt extract (0.3%), peptone (0.5%), glucose (1%), penicillin (50 mg/L), and streptomycin (50 mg/L)), cultured at 30° C. for 48 hours, and secured the microorganism which formed yeast-type colonies instead of fungal spore-type.

For the species analysis of the isolated microorganisms, after culturing each of the microorganisms in 3 mL of YMPS liquid medium with shaking at 30° C. at a rate of 180 rpm for 48 hours, and only cells were recovered by the centrifugation. Genomic DNA was extracted using the i-genomic BYF DNA Extraction Mini Kit (iNtRON Biotechnology Inc., Sungnam, Korea). For the analysis of the nucleotide sequences of ITS1, 5.8S rRNA, ITS2, and 28S rRNA, which are used as most useful markers for the evolutionary phylogenetic study of eukaryotic microorganisms, in the thus-extracted DNA, gene amplification was performed by polymerase chain reaction (PCR) using the primers ITS1 (SEQ ID NO: 1) and LR3R (SEQ ID NO: 2). Additionally, for the analysis of 16S rRNA gene of bacteria, primers 27F (SEQ ID NO: 3) and 1492R (SEQ ID NO: 4) were used. The reaction composition used for the amplification of the nucleotide sequences was template DNA (1 μL), 10 pmol ITS1 (1.5 μL), 10 pmol LR3R (1.5 μL), EX taq buffer (Takara; 5 μL), 2.5 mM dNTP (4 μL), distilled water (36.5 μL), and EX taq DNA polymerase (Takara; 0.5 μL). PCR was performed under the following conditions: denaturation at 95° C. for 5 min; 30 cycles of denaturation at 95° C. for 30 sec, annealing at 55° C. for 30 sec, and polymerization at 72° C. for 1 min 30 sec; and additional reaction at 72° C. for 10 min.

The PCR products in the reaction solution obtained after the PCR reaction were purified using the Solgent PCR purification kit (Solgent, Korea) and the purified PCR products were sent to GenoTech Corp. for nucleotide analysis. For the identification of the microorganisms, the analyzed nucleotide sequences were compared using the Basic Local Alignment Search Tool (BLAST) program provided by the National Center for Biotechnology Information (NCBI).

As a result, various yeast microorganisms were isolated and were confirmed to be species capable of ethanol fermentation (Table 1). Additionally, it was confirmed that G-1, G-2, G-3, 1-2, 2-2, etc., shown in Table 1, are yeasts that are frequently utilized in wine processes, cheese fermentation, etc. In light of the nucleotide sequence homology of their ribosomal DNA, it was confirmed that the ribosomal DNA was isolated from various species of yeast microorganisms ranging from very closely-related species to remotely-related species.

The isolated microorganism colonies were re-inoculated into YMPS solid medium and cultured thereon. As a result, 10 species of yeast strains were isolated from grape skin, 9 species from peach skin, 6 species from palm by-products, and 12 species from palm by-product compost.

TABLE 1

| Sample | Sequence File Name | Length | Closest Relative | Accession No. | Homology (%) |
|---|---|---|---|---|---|
| Grape Skin | G-1 | 634 | *Hanseniaspora uvarum* | FR819702 | 100 |
| | G-2 | 574 | *Hanseniaspora occidentalis* | JX103176 | 99.1 |
| | G-4 | 776 | *Wickerhamomyces anomalus* | KF959845 | 100 |
| | NG-1 | 560 | *Issatchenkia occidentalis* | EF564403 | 99.1 |
| | NG-2 | 535 | *Candida diversa* | HQ149317 | 99.4 |
| | NG-3 | 572 | *Hanseniaspora opuntiae* | DQ872866 | 98.4 |
| | NG-4 | 525 | *Candida diversa* | HQ149317 | 99.6 |
| | NG-5 | 835 | *Kodamaea ohmeri* | KC111449 | 98.9 |
| | NG-6 | 526 | *Candida diversa* | HQ149317 | 99.4 |
| | NG-7 | 725 | *Pichia kudriavzevii* | JQ808005 | 98.7 |
| Peach Skin | NP-1 | 584 | *Pichia fermentans* | FN428873 | 99.0 |
| | NP-2 | 613 | *Starmerella bacillaris* | AY394855 | 99.8 |
| | NP-3 | 827 | *Hanseniaspora uvarum* | AM160628 | 98.2 |
| | NP-4 | 674 | *Pichia kluyveri* | FN667994 | 99.7 |
| | NP-5 | 538 | *Candida* sp. | EF460593 | 99.1 |
| | NP-6 | 536 | *Candida diversa* | HQ149317 | 99.1 |
| | NP-7 | 924 | *Hanseniaspora uvarum* | AM160628 | 98.5 |
| | NP-8 | 1021 | *Hanseniaspora opuntiae* | KC111446 | 98.9 |
| | NP-9 | 1061 | *Candida natalensis* | KC542314 | 100 |
| Palm By-product | 1-1 | 1218 | *Kluyveromyces marxianus* | HQ396523 | 99.2 |
| | 1-2 | 582 | *Pichia norvegensis* | FJ972223 | 99.7 |
| | 2-1 | 576 | *Candida ethanolica* | EF550225 | 98.6 |
| | 2-2 | 619 | *Pichia kudriavzevii* | FR774540 | 99.8 |
| | 2-3 | 603 | *Candida ethanolica* | FM180545 | 98.8 |
| | 2-4 | 573 | *Candida ethanolica* | FM180545 | 98.9 |
| Palm By-product Compost | 1 | 570 | *Candida butyri* | AJ539378 | 99.3 |
| | 2 | 539 | *Cryptococcus laurentii* | FN428921 | 98.7 |
| | 3 | 1060 | *Yamadazyma mexicanum* | JX188248 | 98.4 |
| | 4 | 1191 | *Rhodotorula mucilaginosa* | HE660061 | 96.1 |
| | 5 | 1177 | *Pichia caribbica* | KF728801 | 97.3 |
| | 6 | 577 | *Candida butyri* | AJ539378 | 98.8 |
| | 7 | 561 | *Pichia caribbica* | KF728801 | 98.9 |
| | 8 | 566 | *Pichia caribbica* | KF728801 | 99.5 |
| | 9 | 1019 | *Rhodotorula mucilaginosa* | KF411559 | 96.6 |
| | 14 | 578 | *Candida butyri* | AJ539378 | 99.0 |
| | 15 | 1023 | *Rhodotorula mucilaginosa* | KF411559 | 96.7 |
| | 16 | 1131 | *Candida* sp. | JX188248 | 94.1 |

Example 2. Analysis of Acid Resistance of Isolated Microorganisms

For the selection of microorganisms with acid resistance among the microorganisms isolated in Example 1, the microorganisms were cultured on YPD liquid media (yeast extract (1%), peptone (2%), and glucose (2%)) having a pH adjusted to pH 2.0, 3.0, and 6.0, respectively, at 30° C. at a rate of 180 rpm for 48 hours, and the growth curves were analyzed (FIGS. 1 to 4). As a result, the growth for all of the yeast microorganisms was similar at pH 3.0 and pH 6.0, and differences among microorganisms were confirmed at pH 2.0. Most of the yeast microorganisms isolated from grape skin and peach skin showed a rapid growth at pH 2.0, however, with respect to the microorganisms isolated from palm by-products and palm by-product compost, only a few microorganisms were shown to grow at pH 2.0.

Example 3. Selection of Microorganisms with Lactic Acid Resistance

The 8 kinds of microorganisms which were shown to have excellent acid resistance in Example 2 were selected and their lactic acid resistance was examined The isolated microorganisms were inoculated into YPD liquid media (yeast extract (1%), peptone (2%), and glucose (2%)) containing 0%, 4%, 5%, and 6% lactic acid, and cultured with shaking at 30° C. at a rate of 180 rpm for 48 hours, and the growth curves according to time were analyzed.

As a result, it was confirmed that all of the microorganisms showed a growth in media containing 6% lactic acid, and specifically among them, 2-2, NG1, and NG7 microorganisms showed higher resistance to 6% lactic acid than other microorganisms (FIG. 5). Among the three kinds of microorganisms, the 2-2 and NG7 microorganisms were classified as *Pichia kudriavzevii* microorganisms by the result of nucleotide sequence analysis of ribosomal RNA. However, the 2-2 microorganism showed a homology of 99.8%, having a sequence almost the same as that of the *Pichia kudriavzevii* microorganism, whereas the NG7 microorganism showed a relatively low homology of 98.7%.

Example 4. Selection of Heat Resistance Microorganisms Among the Selected Microorganisms with Acid Resistance The heat resistance was compared among the 2-2, NG1, and NG7 microorganisms, which were selected as microorganisms having high lactic acid resistance in Example 3.

The selected microorganisms were inoculated into YPD liquid media (yeast extract (1%), peptone (2%), and glucose (2%)) at 30° C., 37° C., 42° C., and 50° C., respectively, and cultured with shaking for 48 hours and the growth curves were analyzed. *Kluyveromyces maxianus*, which has heat resistance to high temperature, and *Saccharomyces cerevisiae* were used as control microorganisms.

As a result, it was confirmed that all three selected microorganisms showed an optimal growth at 30° C., the 2-2 microorganism showed a similar growth to that of *Kluyvero-*

*myces maxianus* at 42° C., and in particular, the NG7 microorganism showed a growth even at 50° C. Therefore, it was confirmed that the NG7 microorganism has higher temperature resistance than the 2-2 microorganism, which was classified as a *Pichia kudriavzevii* same as NG7, and the *Kluyveromyces maxianus*, which is known to have heat resistance to high temperature (FIG. 6).

Example 5. Confirmation of Resistance of Isolated Microorganisms to Antibiotics

The antibiotic resistance of the selected three different kinds of microorganisms to various antibiotics was examined. The antibiotics used were zeocin (100 μg/mL), G418 (100 μg/mL), cycloheximide (1 μg/mL), aureobasidin A (0.1 μg/mL), nourseothricin (100 μg/mL), and hygromycin (100 μg/mL). Each of the cell cultures of the isolated microorganisms was dotted on YPD solid medium (yeast extract (1%), peptone (2%), glucose (2%), and agar (2%)) and cultured at 30° C. As a result, it was confirmed that all of the microorganisms had a resistance to zeocin, G418, and cycloheximide, but no resistance to aureobasidin A, nourseothricin, and hygromycin (Table 2).

TABLE 2

| Micro-organism | Zeocin | G418 | Cyclohex-imide | Aureobasidin A | Nourse-othricin | Hygro-mycin |
|---|---|---|---|---|---|---|
| NG1 | + | + | + | − | − | − |
| NG7 | + | + | + | − | − | − |
| 2-2 | + | + | + | − | − | − |

Example 6. Analysis of Sugar-Utilizing Ability of Selected Microorganisms

For the confirmation of the sugar-utilizing abilities of the selected 2-2, NG1, and NG7 microorganisms, API kit analysis (a method for determining the sugar-utilizing ability of a test microorganism based on the change in turbidity after inoculating the test microorganism suspended in minimal medium into the cupules of the kit, where carbohydrates are contained as the sole carbon source) was performed.

As a result, it was confirmed that the sugar that can be utilized by all of the three microorganisms are glucose and N-acetyl-D-glucosamine and that the NG7 microorganism can utilize glycerol unlike other microorganisms (Table 3).

TABLE 3

| | Analysis Items | API 20C AUX | | |
|---|---|---|---|---|
| | | 2-2 | NG1 | NG7 |
| 1 | Control | − | − | − |
| 2 | Glucose assimilation | + | + | + |
| 3 | Glycerol assimilation | − | − | + |
| 4 | 2-Keto-D-gluconate assimilation | − | − | − |
| 5 | Arabinose assimilation | − | − | − |
| 6 | Xylose assimilation | − | − | − |
| 7 | Adonitol assimilation | − | − | − |
| 8 | Xylitol assimilation | − | − | − |
| 9 | Galactose assimilation | − | − | − |
| 10 | Inositol assimilation | − | − | − |
| 11 | Sorbitol assimilation | − | − | − |
| 12 | α-Methyl-D-glucoside assimilation | − | − | − |
| 13 | N-Acetyl-D-glucosamine assimilation | + | + | + |
| 14 | Cellobiose assimilation | − | − | − |
| 15 | Lactose assimilation | − | − | − |
| 16 | Maltose assimilation | − | − | − |

TABLE 3-continued

| | Analysis Items | API 20C AUX | | |
|---|---|---|---|---|
| | | 2-2 | NG1 | NG7 |
| 17 | Saccharose assimilation | − | − | − |
| 18 | Trehalose assimilation | − | − | − |
| 19 | Melezitose assimilation | + | − | − |
| 20 | Raffinose assimilation | − | − | − |
| 21 | Hyphae | − | − | − |

For the confirmation of glycerol-utilizing ability in liquid medium, the three microorganisms were inoculated into YPG liquid media (yeast extract (1%), peptone (2%), and glycerol (2%)) cultured with shaking incubator at 30° C. at a rate of 180 rpm for 48 hours. The growth of the microorganisms was compared using YPD liquid media (yeast extract (1%), peptone (2%), and glucose (2%)) as the control.

As a result, all of the three microorganisms showed similar growth in YPD liquid media. However, in YPG media containing glycerol, all three microorganisms showed a growth but the NG7 microorganism showed a higher growth than the other two microorganisms, and the NG7 microorganism in YPG liquid media also showed a higher growth than in YPD liquid media (FIG. 7).

Since glycerol is generated in a large amount during biodiesel production and is also a carbon source that can be supplied at a reasonable price, the NG7 microorganism is expected to have a large availability for industrial uses.

Example 7. Confirmation of Ethanol Productivity of Selected Microorganisms

The ethanol productivity of the three microorganisms (2-2, NG1, and NG7) selected in Example 6 were examined. Each of the microorganisms cultured in ethanol fermentation medium (glucose (5%), peptone (5 g/L), yeast extract (5 g/L), potassium phosphate (5 g/L), ammonium sulfate (2 g/L), and magnesium sulfate (0.4 g/L)) was inoculated in a concentration of 5% and cultured with shaking in four different conditions (pH 2.0, pH 6.0, 37° C., and 42° C.) at a rate of 100 rpm for 48 hours. *Saccharomyces cerevisiae* and *Kluyveromyces maxianus*, which has heat resistance, were used as control microorganisms.

As a result, it was confirmed that the microorganisms used as control did not show any growth at pH 2.0, but all of the three microorganisms (2-2, NG1, and NG7) showed a growth thereat and produced about 25 g/L of ethanol. In particular, the NG7 microorganism showed the most rapid fermentation rate among them. Additionally, in the case of the NG7 microorganism, it produced about 25 g/L of ethanol at pH 6.0 in about 9 hours, whereas the 2-2 and NG1 microorganisms and *Saccharomyces cerevisiae* produced about 25 g/L of ethanol at pH 6.0 in about 12 hours, and *Kluyveromyces maxianus* in about 36 hours (FIG. 8). Specifically, 2-2, NG1, and NG7 microorganisms exhibited no difference in growth and ethanol fermentation at pH 2.0 and pH 6.0, thus confirming their excellent acid resistance.

Additionally, 2-2 and NG1 microorganisms showed the best growth at 37° C. and produced about 25 g/L of ethanol in about 8 hours. At 42° C., 2-2 and NG1 microorganisms showed a better growth compared to *Kluyveromyces maxianus*, and produced about 25 g/L of ethanol in about 8 hours. In contrast, *Kluyveromyces maxianus* produced about 22 g/L of ethanol in about 15 hours, and *Saccharomyces cerevisiae* and NG1 microorganism produced less than 10 g/L of ethanol (FIG. 9). Additionally, in the case of 2-2 and NG7 microorganisms, they showed significantly excellent growth curves at 42° C. compared to other microorganisms thus confirming their excellent heat resistance (FIG. 9).

From the above results, it was confirmed that the NG7 microorganism has excellent ability of ethanol fermentation in a high-temperature acidic condition, thus confirming that the NG7 microorganism has excellent heat resistance and acid resistance.

As such, the NG7 microorganism was selected as a novel acid-resistant microorganism for producing an organic acid or alcohol, and the microorganism was deposited to the KCTC of the Korean Research Institute of Bioscience and Biotechnology (KRIBB, Korea) on Jun. 17, 2014, under the Accession Number of KCTC18297P. The deposition of the microorganism, based on the Korean deposition, was converted into an international deposition under the Budapest Treaty on Jun. 9, 2015, and assigned the Accession Number of KCTC12840BP.

Example 8. Deletion of PDC1 Gene and Introduction of LDH Gene

In order to block the ethanol biosynthesis pathway of the NG7 microorganism and convert pyruvate into D-lactic acid, the pyruvate decarboxylase (PDC1) gene was replaced with D-lactate dehydrogenase (D-LDH) gene (SEQ ID NO: 19), which is a D-lactic acid-producing enzyme derived from *Lactobacillus plantarum*. An upstream region (500 bp) and a downstream region (500 bp) of PDC1 ORF, and GAPDH promoter from the genomic DNA of the NG7 microorganism were amplified by PCR, and NAT gene was amplified after synthesis. The D-LDH gene was amplified by PCR using the genomic DNA derived from *Lactobacillus plantarum* as a template. The primers used for the PCR are summarized in Table 4 below.

TABLE 4

| SEQ ID NO | Primer | Recognition Site | Sequence (5' -> 3') |
|---|---|---|---|
| 5 | 1 | PDC1 promoter forward direction | ATTTCAGTGCACCATTTTAATTTCTATTGC |
| 6 | 2 | PDC1 promoter reverse direction | TGCAATAATTTTCATATTTTTATGTTTTGC |
| 7 | 3 | LDH forward direction | GCAAAACATAAAAATATGAAAATTATTGCA |
| 8 | 4 | LDH reverse direction | TACATTCAGATGTCATTAGTCAAACTTAAC |
| 9 | 5 | PDC1 terminator forward direction | GTTAAGTTTGACTAATGACATCTGAATGTA |
| 10 | 6 | PDC1 terminator reverse direction | ATCGAAATCTAGCCCGATGGATTGTTTTAG |
| 11 | 7 | GAPDH promoter forward direction | CTAAAACAATCCATCGGGCTAGATTTCGAT |
| 12 | 8 | GAPDH promoter reverse direction | AGACATGGTGAATTCTTTTTGTAATTGTGT |
| 13 | 9 | NAT forward direction | ACACAATTACAAAAAGAATTCACCATGTCT |
| 14 | 10 | NAT reverse direction | CTTGGGAGATAGACTGTCGACTTATGGACA |
| 15 | 11 | PDC ORF downstream forward direction | TGTCCATAAGTCGACAGTCTATCTCCCAAG |
| 16 | 12 | PDC ORF downstream reverse direction | TTAAGCGGCTTTAGAGTTGATTTCATCAGA |
| 17 | 13 | PDC1 promoter forward direction | ATTGTATCCTATCCTATTCGATCCTATTGT |
| 18 | 14 | PDC1 promoter reverse direction | TTGCAAAGACGCAATATTCTCTCTCCCATG |

Each of the amplified genes was connected by overlap extension PCR, and the NG7 microorganism was transformed by introducing the PCR products thereto by electroporation. The transformed microorganism was plated on YPD solid medium containing nourseothricin (NTC; 100 µg/mL) and the transformants were selected therefrom. Transformants were confirmed by PCR using a combination of primer pairs of primer 13 (SEQ ID NO: 17) and primer 4 (SEQ ID NO: 8); primer 7 (SEQ ID NO: 11) and primer 14 (SEQ ID NO: 18); primer 13 and primer 8 (SEQ ID NO: 12); primer 9 (SEQ ID NO: 13) and primer 14; and primer 1 (SEQ ID NO: 5) and primer 12 (SEQ ID NO: 16). As a result, bands were observed in the expected positions. Since the NG7 microorganism is a diploid, there are two copies of PDC1 gene in the microorganism. Two transformants in which NTC gene and D-LDH gene are introduced into the one of the PDC1 gene loci of the two copies were secured (FIG. 10).

The NG7/D-LDH microorganism, prepared by introducing the LDH gene (SEQ ID NO: 19) into one copy of the PDC1 gene as described above, was deposited to the KCTC of the Korean Research Institute of Bioscience and Biotechnology (KRIBB, Korea) on Jun. 17, 2014, under the Accession Number of KCTC18300P, and the deposition was converted into an international deposition under the Budapest Treaty on Jun. 9, 2015, and assigned the Accession Number of KCTC12841BP.

Example 9. Confirmation of Lactic Acid Production by Transformed Microorganisms in which One Copy of PDC1 Gene is Replaced with LDH Gene In order to confirm the LDH activity of the NG7 microorganism (NG7/D-LDH), in which one copy of the PDC1 gene is deleted and D-LDH is expressed, an enzyme solution (0.1 mL) was reacted with a substrate solution (sodium pyruvate; 2.7 mL) and NADH (0.1 mL). Then the absorbance was measured at 340 nm. A wild-type NG7 microorganism was used as a negative control and *Saccharomyces cerevisiae* CEN.PK/D-LDH, which is a recombinant microorganism expressing D-LDH, was used as a positive control.

As a result, it was confirmed that both transformants, i.e., NG7/D-LDH-1 and NG7/D-LDH-2, were shown to have the LDH activity (FIG. 5).

TABLE 5

|  | LDH activity ($\Delta$A340 nm/5 min) |
|---|---|
| Negative Control (NG7 wt) | 0.019 |
| Positive Control (CEN.PK/D-LDH) | 0.078 |
| NG7/D-LDH-1 | 0.222 |
| NG7/D-LDH-2 | 0.238 |

The lactic acid productivities of the two transformed microorganisms, which were confirmed to have the LDH activity, were confirmed. The microorganisms were cultured in YPD liquid media (yeast extract (1%), peptone (2%), and glucose (2%)) at 30° C. at a rate of 180 rpm. The cells were recovered and inoculated into YPD liquid media containing 10% glucose to have an O.D of 10 and cultured at 30° C. at a rate of 80 rpm for 84 hours. In the case of the two transformed microorganisms, it was confirmed that they continuously maintained their growth with time compared to that of the positive control and they also showed a higher amount of glucose consumption.

Additionally, the amounts of lactic acid production of the two microorganisms were examined by HPLC, and the results revealed that they produced lactic acid in an amount of 36.2 g/L and 31.3 g/L, respectively, and ethanol in an amount of 32.6 g/L and 34.2 g/L, respectively (Table 6 and FIG. 11). Since the microorganisms prepared in the present invention still had one remaining copy of the PDC1 gene, ethanol was produced in an amount similar to that of lactic acid. However, it was confirmed that a significant amount of lactic acid was still produced in a condition not adjusting pH.

TABLE 6

|  | Amount of Lactic Acid Production (g/L) | Amount of Ethanol Production (g/L) |
|---|---|---|
| CEN.PK/D-LDH | 12.5 | 47 |
| NG7/D-LDH-1 | 36.2 | 32.6 |
| NG7/D-LDH-2 | 31.3 | 34.2 |

Example 10. Preparation of a Uracil Auxotrophic Microorganism (NG7/$\Delta$ura3)

URA3 gene is a selection marker gene, and at the same time, it is a gene enabling a negative selection in 5-fluoroorotic acid (FOA) medium, thus having an advantage in that the gene can be repeatedly used. For the utilization of the characteristics, first, a uracil auxotrophic NG7 microorganism was prepared.

Since the NG7 microorganism is a diploid, two copies of the URA3 gene were inactivated, respectively. After confirming that the NG7 microorganism has no resistance to nourseothricin (NTC), a disruption cassette using the nourseothricin acetyl transferase (NAT) gene as a selection marker in order to attempt the inactivation of the URA3 gene. An upstream region (500 bp) and a downstream region (500 bp) of URA3 ORF, and GAPDH promoter from the genomic DNA of the NG7 microorganism were amplified by PCR, and NAT gene was amplified after synthesis. Each of the amplified genes was connected by overlap extension PCR, and the NG7 microorganism was subjected to a first transformation by introducing the PCR products thereto by electroporation. The primers used for the PCR are summarized in Table 7 below.

TABLE 7

| SEQ ID NO | Primer | Recognition Site | Sequence (5' -> 3') |
|---|---|---|---|
| 21 | 15 | URA promoter forward direction | GAGGAAACTTCAATCGTCGAAGAAGATAAG |
| 22 | 16 | URA promoter reverse direction | GTTTGTTTGTCAAGGGGGCTAGATTTCGAT |
| 23 | 17 | GAPDH promoter forward direction | ATCGAAATCTAGCCCCCTTGACAAACAAAC |
| 24 | 18 | NTC reverse direction | ATCTTTGTGTAAGAAGTCGACTTATGGACA |
| 25 | 19 | URA3 terminator forward direction | TGTCCATAAGTCGACTTCTTACACAAAGAT |
| 26 | 20 | URA3 terminator forward direction | TACCAAGAAGACGTTCATGTATGTTTCTGT |

The transformed microorganism was plated on YPD solid medium containing NTC (100 μg/mL) and the transformants were selected therefrom. The presence of transformation was confirmed by PCR using primer 15 (SEQ ID NO: 21) and primer 20 (SEQ ID NO: 26). As a result, it was confirmed that the NTC cassette was introduced into the URA3 locus and that one copy of the URA3 gene was still remaining (FIG. 12).

For the inactivation of the remaining copy of the URA3 gene, the NG7 microorganism, in which one copy of the URA3 gene is inactivated was transformed using the same disruption cassette.

The transformed microorganism was plated on solid medium (yeast nitrogen base (6.7 g/L) without amino acid, glucose (2%), agar (2%), uracil (100 μg/mL), and FOA (500 μg/mL)) containing 5-FOA, and the transformants were selected therefrom. Transformats were confirmed by PCR using primers 15 and 20. As a result, it was confirmed that the NTC cassette was properly inserted into the URA3 locus and the URA3 gene was not present (FIG. 13).

Example 11. Deletion of Two Copies of PDC1 Gene and Introduction of LDH Gene Using a Uracil Auxotrophic Selection Marker As confirmed in Example 9, when LDH gene was expressed in a microorganism in which only one copy of the PDC1 gene was deleted, the amount of ethanol production was the same as that of lactic acid. Therefore, for the improvement of the lactic acid productivity, it was attempted to prepare a microorganism in which both copies of the PDC1 gene are deleted to thereby produce only lactic acid while completely blocking the ethanol production pathway.

For the blocking of the ethanol production pathway of the NG7 microorganism and converting pyruvate into lactic acid, the PDC1 gene was replaced with D-lactate dehydrogenase (D-LDH) gene (SEQ ID NO: 19), which is a D-lactic acid-producing enzyme derived from *Lactobacillus plantarum*.

An upstream region (500 bp) and a downstream region (500 bp) of PDC1 ORF, PDC1 terminator (300 bp), and URA promoter-URA ORF-URA terminator (1.5 kb) from the genomic DNA of the NG7 microorganism were amplified by PCR, and D-LDH gene was amplified by PCR using the genomic DNA derived from *Lactobacillus plantarum* as a template. The primers used for the PCR are summarized in Table 8 below.

Each of the amplified genes was connected by overlap extension PCR, and the NG7/Δura3 microorganism was transformed by introducing the PCR products thereto by electroporation. The transformed microorganism was plated on UD solid (yeast nitrogen base (6.7 g/L) without amino acid, glucose (2%), agar (2%), and casamino acid (5 g/L)) and the transformants were selected therefrom. The presence of transformation was confirmed by PCR using a combination of primer pairs of primer 13 (SEQ ID NO: 17) and primer 4 (SEQ ID NO: 8); primer 22 (SEQ ID NO: 28) and primer 23 (SEQ ID NO: 29); primer 1 (SEQ ID NO: 5) and primer 23 (SEQ ID NO: 29); primer 13 and primer 12 (SEQ ID NO: 16); and primer 25 (SEQ ID NO: 31) and primer 26 (SEQ ID NO: 32). As a result, DNA bands were observed in the expected positions, thereby transformants in which LpLDH gene was inserted into each locus of the PDC1 gene, were secured, respectively (FIG. 14).

The NG7Δpdc1/D-LpLDH microorganism, in which the LDH gene (SEQ ID NO: 19) was respectively introduced into each copy of the PDC1 gene as described above, was deposited to the KCTC of the Korean Research Institute of Bioscience and Biotechnology (KRIBB, Korea) on Jun. 2, 2015, under the Accession Number of KCTC18394P, and the deposition was converted into an international deposition under the Budapest Treaty on Jun. 9, 2015, and assigned the Accession Number of KCTC12842BP.

Example 12. Confirmation of Lactic Acid Production without pH Adjustment

In order to confirm the LDH activity of the NG7 microorganism, in which 2 copies of PDC1 gene are deleted and D-LDH is expressed, an enzyme solution (0.1 mL) was reacted with a substrate solution (sodium pyruvate; 2.7 mL) and NADH (0.1 mL), and the absorbance of the resultant was measured at 340 nm. A wild-type NG7 microorganism was used as a negative control and *Saccharomyces cerevisiae* CEN.PK/D-LDH, which is a recombinant microorganism expressing D-LDH, was used as a positive control.

As a result, it was confirmed that the NG7Δpdc1/D-LpLDH transformant was shown to have high LDH activity (Table 9).

TABLE 8

| SEQ ID NO | Primer | Recognition Site | Sequence (5' -> 3') |
|---|---|---|---|
| 27 | 21 | PDC1 terminator reverse direction | AAAGATCGTTGAACAGATGGATTGTTTTAG |
| 28 | 22 | URA promoter forward direction | CTAAAACAATCCATCTGTTCAACGATCTTT |
| 29 | 23 | URA3 terminator reverse direction | CTTGGGAGATAGACTAACACTTAGAATACG |
| 30 | 24 | PDC ORF downstream forward direction | CGTATTCTAAGTGTTAGTCTATCTCCCAAG |
| 31 | 25 | PDC ORF upstream forward direction | TCCCTAGGTACTTATCTGTTTGAAAAGTTA |
| 32 | 26 | PDC ORF downstream reverse direction | GTTGATTTCATCAGATAATTTAGCTTGAGC |

TABLE 9

| | LDH activity (ΔA340 nm/5 min) |
|---|---|
| Negative Control (NG7 wt) | 0.162 |
| Positive Control (CEN.PK/D-LDH) | 0.078 |
| NG7Δpdc1/D-LpLDH | 4.446 |

The lactic acid productivity of the transformed NG7Δpdc1/D-LpLDH microorganism, which was confirmed to have the LDH activity, was confirmed. The microorganism was cultured in YPD liquid medium (yeast extract (1%), peptone (2%), and glucose (2%)) at 30° C. at a rate of 180 rpm. The cells were recovered and inoculated into YPD liquid medium containing 10% glucose to have an absorbance of 10 at $OD_{600}$ and cultured at 30° C. at a rate of 80 rpm for 96 hours in a condition without pH adjustment.

The amount of lactic acid production of the NG7Δpdc1/D-LpLDH microorganism was examined by HPLC, and the result revealed that the microorganism produced lactic acid in an amount of 21.2 g/L, consumed glucose in an amount of 36.5 g/L, but ethanol was not produced (Table 10 and FIG. 15).

TABLE 10

| | Amount of Lactic Acid Production (g/L) | Amount of Glucose Consumption (g/L) | Amount of Ethanol Production (g/L) |
|---|---|---|---|
| NG7Δpdc1/D-LpLDH | 21.2 | 36.5 | 0.3 |

Example 13. Confirmation of Lactic Acid Production According to Various Culture Conditions without pH Adjustment For the establishment of the optimal conditions for lactic acid production by the NG7Δpdc1/D-LpLDH microorganism, the lactic acid productivity was examined under the various rpm conditions and concentrations of cells for inoculation. The experiments were performed at 80 rpm, 120 rpm, 160 rpm, and 180 rpm, and the concentration of the cells for inoculation was in a condition of $OD_{600}$=5 or $OD_{600}$=10. All experiments were performed in conditions without pH adjustment.

First, the amount of lactic acid production of the microorganism was examined when the microorganism was cultured in a concentration of the cells ($OD_{600}$=5) at various rpms. As a result, it was confirmed that the microorganism produced lactic acid in an amount of 17.16 g/L at 80 rpm, 16.99 g/L at 120 rpm, 20.11 g/L at 160 rpm, and 20.06 g/L at 180 rpm (Table 11, FIG. 16).

Additionally, the amount of lactic acid production of the microorganism was examined when the microorganism was cultured in a concentration of the cells ($OD_{600}$=10) at various rpms. As a result, it was confirmed that the microorganism produced lactic acid in an amount of 16.14 g/L at 80 rpm, 18.36 g/L at 120 rpm, 20.01 g/L at 160 rpm, and 19.89 g/L at 180 rpm (Table 12, FIG. 17).

TABLE 11

| rpm | Amount of Lactic Acid Production (g/L) | Amount of Glucose Consumption (g/L) |
|---|---|---|
| 80 | 17.16 | 30.73 |
| 120 | 16.99 | 31.71 |
| 160 | 20.11 | 34.72 |
| 180 | 20.06 | 33.29 |

TABLE 12

| rpm | Amount of Lactic Acid Production (g/L) | Amount of Glucose Consumption (g/L) |
|---|---|---|
| 80 | 16.14 | 29.68 |
| 120 | 18.36 | 32.96 |
| 160 | 20.01 | 34.62 |
| 180 | 19.89 | 33.03 |

Summarizing the results at various conditions, it was confirmed that the concentration of inoculating cells or rpm had little effect on lactic acid productivity in the NG7Δpdc1/D-LpLDH microorganism. However, when the microorganism was cultured at a rate of 160 rpm after adjusting the concentration of inoculating cells at $OD_{600}$=5, the lactic acid production reached the highest level.

Example 14. Confirmation of Lactic Acid Production with pH Adjustment

In order to confirm the effect of pH adjustment of medium on lactic acid production by the NG7Δpdc1/D-LpLDH microorganism, the lactic acid productivity was confirmed by adding calcium carbonate to the medium. Calcium carbonate was added to YPD liquid media containing 10% glucose to a concentration of 1%, 2%, and 3%, respectively, and cultured at 30° C. at a rate of 160 rpm for 100 hours.

As a result, when calcium carbonate was not added the microorganism produced 23.83 g/L of lactic acid and consumed 36.89 g/L of glucose. When 1% calcium carbonate was added, the microorganism produced 40.96 g/L of lactic acid and consumed 59.69 g/L of glucose. When 2% calcium carbonate was added, the microorganism produced 57.22 g/L of lactic acid and consumed 85.21 g/L of glucose. Lastly, when 3% calcium carbonate was added, the microorganism produced 73.09 g/L of lactic acid and consumed 100 g/L g/L of glucose (Table 13, FIG. 18).

TABLE 13

| Calcium Carbonate (%) | Amount of Lactic Acid Production (g/L) | Amount of Glucose Consumption (g/L) |
|---|---|---|
| 0 | 23.83 | 36.89 |
| 1 | 40.96 | 59.69 |
| 2 | 57.22 | 85.21 |
| 3 | 73.09 | 100 |

Additionally, calcium carbonate was added to YPD liquid media containing 15% glucose to a concentration of 3% and 5%, respectively, and cultured at 30° C. at a rate of 160 rpm for 100 hours. When 3% calcium carbonate was added, the microorganism produced 79 g/L of lactic acid and consumed 85 g/L of glucose. When 5% calcium carbonate was added, the microorganism produced 112 g/L of lactic acid and consumed 140 g/L of glucose (Table 14, FIG. 19).

TABLE 14

| Calcium Carbonate (%) | Amount of Lactic Acid Production (g/L) | Amount of Glucose Consumption (g/L) |
|---|---|---|
| 3 | 79 | 85 |
| 5 | 112 | 140 |

From the above experiments, when calcium carbonate was added at various concentration in media, it was confirmed that the productivity of lactic acid increased as the concentration of calcium carbonate increases and that lactic acid productivity can be maximized by an appropriate adjustment of the pH for fermentation.

Example 15. Increase of Lactic Acid Production by Utilization of Glycerol

Since the NG7 microorganism has an excellent glycerol-utilizing ability unlike other yeast microorganisms, the lactic acid productivity of the microorganism in glycerol-containing medium was examined. The lactic acid productivities of the NG7Δpdc1/D-LpLDH microorganism in media containing various glycerol concentrations were compared. The microorganism was inoculated to YPD liquid media (yeast extract (1%), peptone (2%), and glucose (5%), where the glucose was adjusted to 5%), in which glycerol was added to have a concentration of 0 to 10%, to a concentration of $OD_{600}=5$ and cultured at 30° C., at a rate of 160 rpm for 48 hours without pH adjustment.

TABLE 15

| Carbon Source | Amount of Lactic Acid Production (g/L) | Amount of Glucose Consumption (g/L) |
|---|---|---|
| Glucose (5%) | 13.7 | 20 |
| Glucose (5%) + Glycerol (1%) | 17.2 | 24 |
| Glucose (5%) + Glycerol (3%) | 18.1 | 24 |
| Glucose (5%) + Glycerol (5%) | 18.2 | 30 |
| Glucose (5%) + Glycerol (7%) | 20.3 | 27 |
| Glucose (5%) + Glycerol (10%) | 21.3 | 27 |

When glycerol was added to media along with glucose, the amount of glycerol used as a carbon source was very little. However, as the amount of glucose consumption increased in proportion to the increase of the amount of glycerol added thereto, the amount of lactic acid production also increased, and when glycerol in a concentration of 5% or higher was added, the amount of lactic acid production increased by 40% or higher. Such effect is thought to occur because glycerol may help to stabilize the microorganism in an acidic condition or metabolism of glycerol may advantageously act on lactic acid production. Accordingly, for the production of lactic acid, the ability to increase lactic acid productivity by glycerol utilization can provide various advantages as a lactic acid-producing microorganism.

Example 16. Lactic Acid Production of NG7Δpdc1/D-LpLDH Microorganism by Fed-Batch Culture The lactic acid productivity of the NG7Δpdc1/D-LpLDH microorganism by fed-batch culture was examined. The cultivation was performed in a two-step fed-batch culture, in which NG7Δpdc1/D-LpLDH microorganism was inoculated into YPD10 (yeast extract (3%), peptone (1.5%), and glucose (10%)) and cultured at 30° C. at 500 rpm (impeller rotation speed) in an aerobic condition for 12 hours, again supplied with 10% glucose, and in 60 hours thereafter, further supplied with 5% glucose. The pH of the media was maintained at pH 6.0 over the entire fermentation process using NaOH.

As a result, the concentration of lactic acid production was increased up to 120 hours of culture, and the microorganism consumed about 200 g/L of glucose to produce 116 g/L (0.57 g/g) of lactic acid (FIG. 20).

Example 17. Confirmation of Lactic Acid Production by Fed-Batch Culture in a Condition Using a Minimal Amount of a Neutralizing Agent The lactic acid productivity of the NG7Δpdc1/D-LpLDH microorganism by fed-batch culture was examined in an acidic fermentation condition minimizing the use of a neutralizing agent. The NG7Δpdc1/D-LpLDH microorganism was inoculated into YPD10 (yeast extract (3%), peptone (1.5%), glucose (10%), and glycerol (2%)) and cultured at 30° C. at 700 rpm (impeller rotation speed) to go through with cell growth stage for 18 hours, and cultured for 5 hours after adjusting the impeller rotation speed to 400 rpm to convert into an anaerobic condition, and supplied with 10% glucose and the pH of the media was maintained at pH 5.5 using NaOH. To proceed further with an acid fermentation by the natural decrease of pH due to the lactic acid produced during the fermentation process, pH was not adjusted any more after 35 hours.

As a result, the microorganism showed a high productivity of 5 g/L/hr in the stage of pH adjustment, but in the stage of without pH adjustment, the microorganism reduced lactic acid production and finally 118 g/L of lactic acid was obtained. In an anaerobic condition, the microorganism did not grow but continued to produce lactic acid for 20 hours or more, and the pH of the final fermentation medium was 4.6.

Accordingly, it was confirmed that the microorganism provided in the present invention can maximize lactic acid production (118 g/L) by adjusting the amount of a neutralizing agent to be used during fermentation, reduce the cost for a post-process by acidifying the pH of the final fermentation liquid, and minimize the production of gypsum, a waste product (FIG. 21).

The above results suggest that the *Pichia kudriavzevii* NG7 microorganism with acid resistance and heat resistance, which was newly isolated and identified in the present invention, can be used as a microorganism for producing various useful organic acids and/or alcohols using various raw materials for sugar.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A modified *Pichia* kudriavzevii NG7 microorganism having acid resistance and heat resistance, wherein said modified *Pichia* kudriavzevii NG7 microorganism is made by introducing an activity of lactate dehydrogenase to a *Pichia* kudriavzevii NG7 microorganism deposited under the Accession Number KCTC12840BP by heterologous expression of lactate dehydrogenase of *Lactobacillus* and wherein said modified *Pichia* kudriavzevii NG7 microorganism produce more lactic acid compare to unmodified *Pichia* kudriavzevii NG7 microorganism deposited under the Accession Number KCTC12840BP.

2. The modified microorganism of claim 1, wherein an activity of orotidine 5'-phosphate decarboxylase (URA3) is inactivated.

3. A modified *Pichia* kudriavzevii NG7 microorganism deposited under the Accession Number KCTC12841BP.

4. The modified microorganism of claim 1, wherein the microorganism has an ability to use glycerol as a carbon source.

5. The modified microorganism of claim 2, wherein an activity of pyruvate decarboxylase is inactivated.

6. A modified *Pichia kudriavzevii* NG7 microorganism deposited under the Accession Number KCTC12842BP.

7. A composition comprising the modified microorganism of claim 1 and a carbon source.

8. The composition of claim 7, wherein the composition further comprises glycerol.

9. A method for producing an organic acid or alcohol, comprising culturing the modified microorganism of claim 1 in medium.

10. The method of claim 9, wherein the organic acid is lactic acid.

11. The method of claim 9, wherein the medium comprises glycerol.

12. The method of claim 9, wherein the cultivation is performed in a condition without adding a neutralizing agent.

13. A modified *Pichia kudriavzevii* NG7 microorganism having acid resistance and heat resistance, wherein an activity of orotidine 5'-phosphate decarboxylase (URA3) is inactivated in a *Pichia kudriavzevii* NG7 microorganism deposited under the Accession Number KCTC12840BP.

* * * * *

SEQUENCE LISTING

<160> NUMBER OF SEQ ID NOS: 32

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      ITS1 primer

<400> SEQUENCE: 1
tccgtaggtg aacctgcgg                                                19

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      LR3R primer

<400> SEQUENCE: 2
ggtccgtgtt tcaagac                                                  17

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      27F primer

<400> SEQUENCE: 3
agagtttgat cctggctcag                                               20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      1492R primer

<400> SEQUENCE: 4
ggttaccttg ttacgactt                                                19

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 1

<400> SEQUENCE: 5
atttcagtgc accattttaa tttctattgc                                    30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 2

<400> SEQUENCE: 6
tgcaataatt ttcatatttt tatgttttgc                                    30

```
<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 3

<400> SEQUENCE: 7
gcaaaacata aaaatatgaa aattattgca                                       30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 4

<400> SEQUENCE: 8
tacattcaga tgtcattagt caaacttaac                                       30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 5

<400> SEQUENCE: 9
gttaagtttg actaatgaca tctgaatgta                                       30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 6

<400> SEQUENCE: 10
atcgaaatct agcccgatgg attgttttag                                       30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 7

<400> SEQUENCE: 11
ctaaaacaat ccatcgggct agatttcgat                                       30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 8

<400> SEQUENCE: 12
agacatggtg aattcttttt gtaattgtgt                                       30
```

```
<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 9

<400> SEQUENCE: 13
acacaattac aaaaagaatt caccatgtct                                          30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 10

<400> SEQUENCE: 14
cttgggagat agactgtcga cttatggaca                                          30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 11

<400> SEQUENCE: 15
tgtccataag tcgacagtct atctcccaag                                          30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 12

<400> SEQUENCE: 16
ttaagcggct ttagagttga tttcatcaga                                          30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 13

<400> SEQUENCE: 17
attgtatcct atcctattcg atcctattgt                                          30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 14

<400> SEQUENCE: 18
ttgcaaagac gcaatattct ctctcccatg                                          30
```

<210> SEQ ID NO 19
<211> LENGTH: 999
<212> TYPE: DNA
<213> ORGANISM: Lactobacillus plantarum
<220> FEATURE:
<221> NAME/KEY: gene
<222> LOCATION: (1)..(999)
<223> OTHER INFORMATION: lactate dehydrogenase

<400> SEQUENCE: 19

| | | | | | |
|---|---|---|---|---|---|
| atgaaaatta | ttgcatatgc | tgtacgtgat | gacgaacgtc | cattcttcga | tacttggatg | 60 |
| aaagaaaacc | cagatgttga | agttaaatta | gttccagaat | tacttactga | agacaacgtt | 120 |
| gacttagcta | aaggcttcga | cggtgccgat | gtataccaac | aaaaggacta | tactgctgaa | 180 |
| gtattgaaca | agttagccga | cgaaggggtt | aagaacatct | ctcttcgtaa | cgttggtgtt | 240 |
| gataacttgg | acgttcctac | tgttaaagca | cgtggcttaa | acatttctaa | cgtacctgca | 300 |
| tactcaccaa | atgcgattgc | tgaattatca | gtaacgcaat | tgatgcaatt | attacgtcaa | 360 |
| accccattgt | tcaataagaa | gttagctaag | caagacttcc | gttgggcacc | agatattgcc | 420 |
| aaggaattaa | acaccatgac | tgttggtgtt | atcggtactg | gtcggattgg | ccgtgctgcc | 480 |
| atcgatattt | tcaaaggctt | cggcgctaag | gttatcggtt | acgatgttta | ccggaatgct | 540 |
| gaacttgaaa | aggaaggcat | gtacgttgac | accttggacg | aattatacgc | ccaagctgat | 600 |
| gttatcacgt | tacacgttcc | tgcattgaag | gataactacc | acatgttgaa | tgcggatgcc | 660 |
| ttcagcaaga | tgaaagatgg | cgcctacatc | ttgaactttg | ctcgtgggac | actcatcgat | 720 |
| tcagaagact | tgatcaaagc | cttagacagt | ggcaaagttg | ccggtgccgc | tcttgatacg | 780 |
| tatgaatacg | aaactaagat | cttcaacaaa | gaccttgaag | gtcaaacgat | tgatgacaag | 840 |
| gtcttcatga | acttgttcaa | ccgcgacaat | gttttgatta | caccacatac | ggctttctac | 900 |
| actgaaactg | ccgttcacaa | catggtgcac | gtttcaatga | acagtaacaa | acaattcatc | 960 |
| gaaactggta | agctgatac | gcaagttaag | tttgactaa | | | 999 |

<210> SEQ ID NO 20
<211> LENGTH: 1689
<212> TYPE: DNA
<213> ORGANISM: Pichia kudriavzevii
<220> FEATURE:
<221> NAME/KEY: gene
<222> LOCATION: (1)..(1689)
<223> OTHER INFORMATION: Pyruvate Decarboxylase

<400> SEQUENCE: 20

| | | | | | |
|---|---|---|---|---|---|
| atgactgaca | aaatctccct | aggtacttat | ctgtttgaaa | agttaaagga | agcaggctct | 60 |
| tattccatct | ttggtgttcc | tggtgatttc | aatttggcat | tgttggacca | cgttaaggaa | 120 |
| gttgaaggca | ttagatgggt | cggtaacgct | aacgagttga | atgccggcta | cgaagctgat | 180 |
| ggttatgcaa | gaatcaatgg | atttgcatcc | ctaatcacca | cctttggtgt | cggtgaattg | 240 |
| tctgccgtca | atgccattgc | aggttcttat | gctgaacacg | tcccattgat | ccatattgtt | 300 |
| ggtatgcctt | ccttgtctgc | tatgaagaac | aacttgttgt | tacaccatac | cttgggtgac | 360 |
| acaagattcg | acaacttcac | cgaaatgtca | aagaaaatca | gtgcaaaggt | tgagattgtt | 420 |
| tacgatttgg | aatcagctcc | aaaattaatt | aataacttga | ttgaaccgc | ttatcacaca | 480 |
| aagagaccag | tctacttggg | acttcctcc | aactttgctg | atgaattggt | tccagcggca | 540 |
| ttagttaagg | aaaacaagtt | acatttagaa | gaacctctaa | caaccccgt | tgctgaagaa | 600 |
| gaattcattc | ataacgttgt | tgaaatggtc | aagaaggcag | aaaaaccaat | cattctcgtt | 660 |

```
gacgcttgtg ctgcaagaca taacatttct aaggaagtga gagagttggc taaattgact    720
aaattccctg tcttcaccac cccaatgggt aaatctactg ttgatgaaga tgatgaagaa    780
ttctttggct tatacttggg ttctctatct gctccagatg ttaaggacat tgttggccca    840
accgattgta tcttatcctt aggtggttta ccttctgatt tcaacaccgg ttccttctca    900
tatggttaca ctactaagaa tgtcgtttat gaaaacttga tgatgaaggg cgcagtccaa    960
agattgatca gcgaattgaa gaatattaag tattccaatg tctcaactTT atctccacca    1020
aaatctaaat ttgcttacga atctgcaaag gttgctccag aaggtatcat cactcaagat    1080
tacctgtgga agagattatc ttacttctta aagccaagag atatcattgt cactgaaact    1140
ggtacttcct cctttggtgt cttggctacc cacttaccaa gagattcaaa gtctatctcc    1200
caagtcttat ggggttccat tggtttctcc ttaccagctg cagttggtgc tgcatttgct    1260
gctgaagatg cacacaaaca aactggcgaa caagaaagaa gaactgtttt gtttattggt    1320
gatggttctt tacaattgac tgtccaatca atctcagatg ctgcaagatg aacatcaag    1380 ccatacatct tcatcttaaa caacagaggt tacactatcg aaaagttgat ccacggtcgt    1440
catgaggact acaaccaaat tcaaccatgg gatcaccaat tgttattgaa gctctttgct    1500
gacaagaccc aatatgaaaa ccatgttgtt aaatccgcta agacttgga cgcttttgatg    1560 aaggatgaag cattcaacaa ggaagataag attagagtca ttgaattatt cttggatgaa    1620
ttcgatgctc cagaaatctt ggttgctcaa gctaaattat ctgatgaaat caactctaaa    1680
gccgcttaa                                                           1689

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 15

<400> SEQUENCE: 21
gaggaaactt caatcgtcga agaagataag                                      30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 16

<400> SEQUENCE: 22
gtttgtttgt caaggggct agatttcgat                                       30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 17

<400> SEQUENCE: 23
atcgaaatct agccccttg acaaacaaac                                       30

<210> SEQ ID NO 24
<211> LENGTH: 30
<212> TYPE: DNA
```

<213> ORGANISM: Artificial Sequence
<220> FEATURE:
<223> OTHER INFORMATION: Description of Artificial Sequence: Synthetic
     primer 18

<400> SEQUENCE: 24
atctttgtgt aagaagtcga cttatggaca                                30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
     primer 19

<400> SEQUENCE: 25
tgtccataag tcgacttctt acacaaagat                                30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
     primer 20

<400> SEQUENCE: 26
taccaagaag acgttcatgt atgtttctgt                                30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
     primer 21

<400> SEQUENCE: 27
aaagatcgtt gaacagatgg attgttttag                                30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
     primer 22

<400> SEQUENCE: 28
ctaaaacaat ccatctgttc aacgatcttt                                30

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
     primer 23

<400> SEQUENCE: 29
cttgggagat agactaacac ttagaatacg                                30

<210> SEQ ID NO 30
<211> LENGTH: 30
<212> TYPE: DNA
<213> ORGANISM: Artificial Sequence

```
<220> FEATURE:
<223> OTHER INFORMATION: Description of Artificial Sequence: Synthetic
      primer 24

<400> SEQUENCE: 30
cgtattctaa gtgttagtct atctcccaag                                        30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 25

<400> SEQUENCE: 31
tccctaggta cttatctgtt tgaaaagtta                                        30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer 26

<400> SEQUENCE: 32
gttgatttca tcagataatt tagcttgagc                                        30
```